(12) United States Patent
Wu et al.

(10) Patent No.: US 11,518,730 B2
(45) Date of Patent: Dec. 6, 2022

(54) POLYMER COMPOSITIONS FOR SELF-ASSEMBLY APPLICATIONS

(71) Applicant: RIDGEFIELD ACQUISITION, Luxembourg (LU)

(72) Inventors: Hengpeng Wu, Hillsborough, NJ (US); Jian Yin, Bridgewater, NJ (US); Guanyang Lin, Whitehouse Station, NJ (US)

(73) Assignee: Merck Patent GmbH, Darmstadt (DE)

( * ) Notice: Subject to any disclaimer, the term of this patent is extended or adjusted under 35 U.S.C. 154(b) by 677 days.

(21) Appl. No.: 16/323,102

(22) PCT Filed: Aug. 16, 2017

(86) PCT No.: PCT/EP2017/070726
§ 371 (c)(1),
(2) Date: Feb. 4, 2019

(87) PCT Pub. No.: WO2018/033559
PCT Pub. Date: Feb. 22, 2018

(65) Prior Publication Data
US 2019/0161570 A1 May 30, 2019

Related U.S. Application Data

(60) Provisional application No. 62/376,793, filed on Aug. 18, 2016.

(51) Int. Cl.
| | | |
|---|---|---|
| C08F 293/00 | (2006.01) | |
| G03F 7/00 | (2006.01) | |
| C07C 69/76 | (2006.01) | |
| C09D 133/14 | (2006.01) | |
| C08F 220/30 | (2006.01) | |
| C08F 212/08 | (2006.01) | |
| G03F 7/16 | (2006.01) | |
| G03F 7/20 | (2006.01) | |

(52) U.S. Cl.
CPC ............ *C07C 69/76* (2013.01); *C08F 212/08* (2013.01); *C08F 220/303* (2020.02); *C08F 293/00* (2013.01); *C09D 133/14* (2013.01); *G03F 7/0002* (2013.01); *G03F 7/0035* (2013.01); *G03F 7/168* (2013.01); *G03F 7/2037* (2013.01); *G03F 7/70141* (2013.01); *C07C 2602/06* (2017.05); *C08F 2810/20* (2013.01)

(58) Field of Classification Search
CPC .... G03F 7/0002; G03F 7/0388; C08F 293/00; C08F 297/04
See application file for complete search history.

(56) References Cited

U.S. PATENT DOCUMENTS

| | | |
|---|---|---|
| 3,161,630 A | 12/1964 | Quilby et al. |
| 3,285,949 A | 11/1966 | Siebert |
| 3,285,959 A | 11/1966 | McFarlane |
| 3,474,054 A | 10/1969 | White |
| 3,919,077 A | 11/1975 | Whitehurst |
| 4,200,729 A | 4/1980 | Calbo |
| 4,251,665 A | 2/1981 | Calbo |
| 4,698,394 A | 10/1987 | Wong |
| 5,136,029 A | 8/1992 | Furukawa et al. |
| 5,187,019 A | 2/1993 | Calbo et al. |
| 5,446,125 A | 8/1995 | Honda et al. |
| 5,674,662 A | 10/1997 | Szmanda et al. |

(Continued)

FOREIGN PATENT DOCUMENTS

| | | |
|---|---|---|
| CA | 1293090 C | 12/1991 |
| EP | 0227124 A2 | 7/1987 |

(Continued)

OTHER PUBLICATIONS

Eungnak Han et al., "Photopatternable Imaging Layers for Controlling Block Copolymer Microdomain Orientation", Advanced Materials Vo. 19, pp. 4448-pp. 4452 (2007).
Craig J. Hawker et al., "Facile Synthesis of Block Copolymers for Nanolithographic Applications", Polymer Preprints vol. 46(2), pp. 239-pp. 240 (2005).
Craig J. Hawker et al., "Initiating Systems for Nitroxide-Mediated "Living" Free Radical Polymerizations: Synthesis and Evaluation", Macromolecules Vo. 29 No. 16, pp. 5245-pp. 5254 (1996).

(Continued)

*Primary Examiner* — Daborah Chacko-Davis
(74) *Attorney, Agent, or Firm* — Francis M. Houlihan

(57) ABSTRACT

The present invention relates to a composition comprises at least one random copolymer having at least one repeat unit of structure (1), The present invention also relates to novel processes for forming patterns using this novel crosslinked layer on a substrate by enable a film of a block copolymer coated on the novel crosslinked layer to undergo self-assembly.

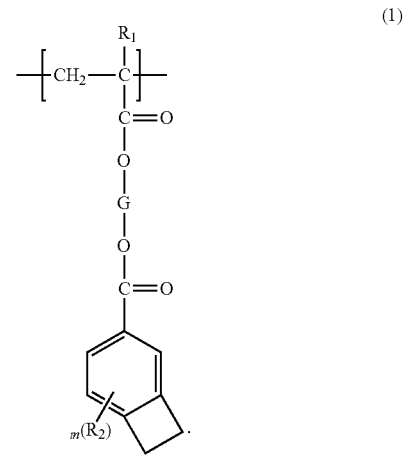

29 Claims, 4 Drawing Sheets

(56) References Cited

U.S. PATENT DOCUMENTS

| | | | |
|---|---|---|---|
| 5,929,204 A | 7/1999 | Noguchi et al. | |
| 6,512,020 B1 | 1/2003 | Asakura et al. | |
| 7,138,490 B2 | 11/2006 | Nakanishi et al. | |
| 7,265,785 B2 | 9/2007 | Hamasaki | |
| 7,282,551 B2 | 10/2007 | Hoff et al. | |
| 7,411,053 B2 | 8/2008 | Harruna et al. | |
| 7,471,614 B2 | 12/2008 | Frommer et al. | |
| 7,521,094 B1 | 4/2009 | Cheng et al. | |
| 7,560,141 B1 | 7/2009 | Kim et al. | |
| 7,790,350 B2 | 9/2010 | Breyta et al. | |
| 7,846,502 B2 | 12/2010 | Kim et al. | |
| 8,017,194 B2 | 9/2011 | Colburn et al. | |
| 8,080,615 B2 | 12/2011 | Millward | |
| 8,133,534 B2 | 3/2012 | Stoykovich et al. | |
| 8,168,284 B2 | 5/2012 | Nealey et al. | |
| 8,226,838 B2 | 7/2012 | Cheng et al. | |
| 8,309,278 B2 | 11/2012 | Yang et al. | |
| 8,323,458 B2 | 12/2012 | O'Connor et al. | |
| 8,362,179 B2 | 1/2013 | Gopalan et al. | |
| 8,491,965 B2 | 7/2013 | Cheng et al. | |
| 8,623,458 B2 | 1/2014 | Cheng et al. | |
| 8,653,211 B2 | 2/2014 | Kang et al. | |
| 8,686,109 B2 | 4/2014 | Yin et al. | |
| 8,691,925 B2 | 4/2014 | Wu et al. | |
| 8,795,539 B2 | 8/2014 | Lee et al. | |
| 8,835,581 B2 | 9/2014 | Wu et al. | |
| 8,859,191 B2 | 10/2014 | Matsumura et al. | |
| 8,999,492 B2 | 4/2015 | Millward et al. | |
| 9,005,756 B2 | 4/2015 | Kim et al. | |
| 9,040,659 B2 | 5/2015 | Yin et al. | |
| 9,093,263 B2 | 7/2015 | Wu et al. | |
| 9,109,086 B2 | 8/2015 | Tang | |
| 9,123,541 B2 | 9/2015 | Xu et al. | |
| 9,157,008 B2 | 10/2015 | Willson et al. | |
| 9,183,870 B2 | 11/2015 | Nealey et al. | |
| 9,291,909 B2 | 3/2016 | Wu et al. | |
| 9,490,117 B2 | 11/2016 | Park et al. | |
| 9,574,104 B1 | 2/2017 | Kim et al. | |
| 2009/0286927 A1 | 11/2009 | Sodergard et al. | |
| 2010/0124629 A1 | 5/2010 | Gopalan et al. | |
| 2011/0014420 A2 | 1/2011 | Gopalan et al. | |
| 2013/0012618 A1 | 1/2013 | Hiro et al. | |
| 2014/0193754 A1 | 7/2014 | Wu et al. | |
| 2014/0335324 A1 | 11/2014 | Kim et al. | |
| 2014/0342290 A1 | 11/2014 | Wu et al. | |
| 2015/0197594 A1 | 7/2015 | Xu et al. | |
| 2016/0237307 A1* | 8/2016 | Cheng | C09D 125/18 |

FOREIGN PATENT DOCUMENTS

| | | |
|---|---|---|
| EP | 1095711 A2 | 2/2001 |
| EP | 2949702 A1 | 12/2015 |
| GB | 715913 A | 9/1954 |
| JP | 58-225103 | 12/1983 |
| JP | S63501157 A | 4/1988 |
| JP | 2003-048929 A | 2/2003 |
| JP | 2003-238682 A | 8/2003 |
| JP | 2003-287882 A | 10/2003 |
| JP | 2008-088368 A | 4/2008 |
| JP | 2010-260883 A | 11/2010 |
| JP | 2011-018778 A | 1/2011 |
| JP | 2015130508 A | 7/2015 |
| JP | 2018538382 A | 12/2018 |
| WO | 1987-05303 | 9/1987 |
| WO | 2008/097736 A1 | 8/2008 |
| WO | 2012/022390 A1 | 2/2012 |
| WO | 2013/156240 A1 | 10/2012 |
| WO | 2012/161106 A1 | 11/2012 |
| WO | 2013/050338 A1 | 4/2013 |
| WO | 2013/160027 A1 | 10/2013 |
| WO | 2017-064199 A1 | 4/2017 |

OTHER PUBLICATIONS

E. Huang et al., "Using Surface Active Random Copolymers to Control the Domain Orientation in Diblock Copolymer Thin Films", Macromolecules vol. 31 No. 22., pp. 7641-pp. 7650 (1998).

Yoojin Kim et al., "The Dramatic Effect of Architecture on the Self-Assembly of Block Copolymers at Interfaces", Langmuir vol. 21 No. 23, pp. 10444-pp. 10458 (2005).

Julie M. Leiston-Belanter et al., "A Thermal and Manufacturable Approach to Stabilized Diblock Copolymer Templates", Macromolecules vol. 38 No. 18, pp. 7676-pp. 7683 (2005).

Du Yeol Ryu et al., "Surface Modification with Cross-Linked Random Copolymers: Minimum Effective Thickness", Macromolecules vol. 40 No. 12, pp. 4296-pp. 4300 (2007).

International Search Report, PCT/EP2017/070726, dated Nov. 16, 2017, corresponds to U.S. Appl. No. 16/323,102.

Junxiao Yang, et al., "Recent Progress in Benzocyclobutene Related Polymers", InTech, Chapter 9, Sep. 12, 2012, pp. 201-222.

Drockenmuller et al. "Covalent Stabilization of Nanostructures: Robust Block Copolymer Templates from Novel Thermoreactive Systems", Published online (Sep. 2004) in Wiley InterScience (www.interscience.wiley.com), p. 1028-1037.

Joy Y. Cheng et al., "Templated Self-Assembly of Block Copolymers: Effect of Substrate Topography", Adv. Mater. vol. 5 No. 19, pp. 1599-pp. 1602 (2003).

Form PCT/ISA/220, Form PCT/ISA/210, and Form PCT/ISA/237 dated Feb. 26, 2013 for PCT/IB2012/001905, which corresponds to U.S. Appl. No. 13/164,869.

Joona Bang et al., "Facile Routes to Patterned Surface Neutralization Layers for Block Copolymer Lithography", Advanced Materials vol. 19, pp. 4552-pp. 4557 (2007).

Christopher N. Bates et al., "Single- and Dual-Component Cross-Linked Polymeric Surface Treatments for Controlling Block Copolymer Orientation", Polymer Preprints vol. 52(1), pp. 181-pp. 182 (2011).

G. J. Kellogg et al., "Observed Surface Energy Effects in Confined Diblock Copolymers", The American Physical Society vol. 76 No. 14, pp. 2503-pp. 2506 (1996).

Yoojin Kim et al., "Effect of Architecture on the Self-Assembly of Block Copolymers at Interfaces: Linear-nanoparticle vs. Linear AB Diblocks", Polymeric Materials: Science & Engineering Vo. 92, pp. 399-pp. 400 (2005).

P. Mansky et al., "Controlling Polymer-Surface Interactions with Random Copolymer Brushes", Science Magazine vol. 275, pp. 1458-pp. 1460 (1997).

Ricardo Ruiz et al., "Density Multiplication and Improved Lithography by Directed Block Copolymer Assembly", Science Magazine vol. 321, pp. 936-pp. 939 (2008).

Toru Yamaguchi et al., "Resist-Pattern Guided Self-Assembly of Symmetric Diblock Copolymer", Journal of Photopolymer Science and Technology vol. 19 No. 3, pp. 385-pp. 388 (2006).

Toru Yamaguchi et al., "Two-Dimentional Patterning of Flexible Designs with High Half-Pitch Resolution by Using Block Copolymer Lithography", Advanced Materials vol. 20, pp. 1684-pp. 1689 (2008).

Yuanlie Yu et al., "The synthesis of novel fluorine-containing random polymer and application in modification of solid surfaces", Surface & Coatings Technology 205, pp. 205-pp. 212 (2010).

Machine Language English Abstract from JPO of JP 58-225103 A, Dated Dec. 27, 1983.

Machine Language English Abstract and Translation from JPO of JP 2013-8951 A, which is equivalent to WO 2012/161106 A1, dated Jan. 10, 2013.

Form PCT/ISA/220, Form PCT/ISA/210, and Form PCT/ISA/237 dated Jul. 11, 2013 for PCT/EP2013/053548, which corresponds to U.S. Appl. No. 13/416,669.

Form PCT/ISA/220, Form PCT/ISA/210, and Form PCT/ISA/237 dated Aug. 28, 2013 for PCT/EP2013/001423, which corresponds to U.S. Appl. No. 13/492,125.

(56) References Cited

OTHER PUBLICATIONS

Koji Asakawa et al., "Nanopatterning with Microdomains of Block Copolymers using Reactive-Ion Etching Selectivity", Jpn. J. Appl. Phys. vol. 41 Part 1 No. 10, pp. 6112-pp. 6118 (2002).
C. T. Black et al., "Integration of self-assembled diblock copolymers for semiconductor capacitor fabrication," Applied Physics Letters vol. 79 No. 3, pp. 409-pp. 411 (2001).
Kenneth C. Caster, "Applications of Polymer Brushes and Other Surface-Attached Polymers", Polymer Brushes Part 17, pp. 331-370 (2004).
Ghislain David et al., "Synthesis of .alpha.,.omega.-Phosponate Polysterene via Dead End Polymerization, Phosporus, Sulfur, and Silicon", Phosphorus, Sulfur, and Silicon vol. 179 No. 12, pp. 2627-pp. 2634 (2004).
Iain E. Dunlop, "Interactions Between Polymer Brushes: Varying the Number of End-Attaching Groups", Macromol. Chem. Phys. vol. 205, pp. 2443-pp. 2450 (2004).
Atsushi Hieno et al., "Quick Formation of DSA Neutralization Polymer Layer Attached by Reactive Self-Assembled Monolayer," J. Photopol. Sci. Tech. vol. 25 No. 1, pp. 73-pp. 76 (2012).
Shengxiang Ji et al., "Preparation of Neutral Wetting Brushes for Block Copolymer Films from Homopolymer Blends", Advanced Materials vol. 20, pp. 3054-pp. 3060 (2008).
Bokyung Kim et al., "Dewetting of PMMA on PS-Brush Substrates", Macromolecules vol. 42 No. 20, pp. 7919-7923 (2009).
Bong Hoon Kim et al.; The Synthesis of Randum Brush for Nanostructure of Block Copolymer, Macromol. Symp., vol. 249-250, pp. 303-306 (2007).
Bumjoon J. Kim et al., "Importance of End-Group Structure in Controlling the Interfacial Activity of Polymer-Coated Nanoparticles", Macromolecules vol. 40 No. 6, pp. 1796-1798 (2007).
Massimo Lazzari et al., "Methods for the Alignment and the Large-scale Ordering of Block Copolymer Morphologies," Block Copolymers in Nanoscience, Edited by M. Lazzari, G. Liu, and S. Lecommandoux, Copyright .COPYRGT. 2006 Wiley-VCH Verlag GmbH & Co. KGaA, Weinheim, pp. 191-pp. 231.
Machine Language English Abstract of WO2012-161106A1, Nov. 29, 2012.
Mao-Peng Lin et al., "Photocrosslinking of Polymers Containing Cationically Polymerizable Groups in the Side-Chain by Sulfonium Salts," Journal of Polymer Science Part A: Polymer Chemistry vol. 30 Issue 5, pp. 933-pp. 936, (1992).
Nancy A. Listigovers et al., "Narrow Polydispersity Diblock and Triblock Copolymers of Alkyl Acrylates by a "Living" Stable Free Radical Polymerization", Macromolecules vol. 29 No. 27, pp. 8992-pp. 8993 (1996).
Hui Liu et al., "Random Poly(methyl methacrylate-co-styrene) Brushes by ATRP to Create Neutral Surfaces for Block Copolymer Self-Assembly," Macromol. Chem. Phys. vol. 213, pp. 108-pp. 115 (2012).
Holger Merlitz, "Surface Instabilities of Monodisperse and Densely Grafter Polymer Brushes", Macromolecules vol. 41 No. 13, pp. 5070-pp. 5072 (2008).
Hironobu Murata et al., "Synthesis of Functionalized Polymer Monolayers from Active Ester Brushes", Macromolecules vol. 40 No. 15, pp. 5497-pp. 5503 (2007).
Timothy E. Patten et al., "Atom Transfer Radical Polymerization and the Synthesis of Polymeric Materials", Adv. Mater. vol. 10 Issue 12, pp. 901-pp. 915 (1998).
R. P. Quirk et al., "Thermoplastic Elastomers 2nd Edition", Hanser/Gardner Publications, pp. 74-pp. 78 (1996).

Du Yeol Ryu et al., "Cylindrical Microdomain Orientation of PS-b-PMMA on the Balanced Interfacial Interactions: Composition Effect of Block Copolymers," Macromolecules vol. 42 No. 13, pp. 4902-pp. 4906 (2009).
I. E. Serhatli, "Synthesis of hybrid liquid crystalline block copolymers by combination of cationic or promoted cationic and free-radical polymerizations", Polymer Bulletin vol. 34, pp. 539-pp. 546 (1995).
Kazuo Sugiyama et al., "Preparation of surface-modified polysterene microspheres by an azo-initiator having analogous structure to the head group of phosphatidylcholine", Macromol. Chem. Phys. vol. 195, pp. 1341-pp. 1352 (1994).
T. Thurn-Albrecht et al., "Ultrahigh-Density Nanowire Arrays Grown in Self-Assembled. Diblock Copolymer Templates", Science vol. 290, pp. 2126-pp. 2129 (2000).
Nathan D. Jamagin et al., PS-b-PHOST as a High .sub.x Block Copolymers for Directed Self Assembly: Optimnization of Underlayer and Solvent Anneal Processes, SPIE vol. 8680, pp. 86801X-1-pp. 86801X-1 (2013).
English Abstract of JP2015-130508A, Jul. 16, 2015.
English translation of Japanese Office Action, Application No. 2019-508886 dated Aug. 17, 2021.
Form PCT/ISA/220, Form PCT/ISA/210, Form PCT/ISA/237 dated Jan. 14, 2015 for PCT/EP2014/070391, which corresponds to U.S. Appl. No. 14/039,809.
Form PCT/ISA/220, Form PCT/ISA/210, and Form PCT/ISA/237 dated Feb. 10, 2015 for PCT/EP2014/076849, which corresponds to U.S. Appl. No. 14/107,325.
Du Yeol Ryu et al., "A Generalized Approach to the Modification of Solid Surfaces", Science vol. 308, pp. 236-pp. 239 (2005).
Machine Language English Abstract of JP 2003-489929 A, Feb. 21, 2003.
Machine Language English Abstract of WO2012-022390A1, Feb. 23, 2012.
Toru Yamaguchi et al., "Resist-Pattern Guided Self-Assembly of Symmetric Diblock Copolymer", Journal of Photopolymer Science and Technology vol. 19 No. 3, pp. 385-pp. 388 (2006). **Reference cited in previously submitted IDS, however, omitted to upload reference.
Machine English Translation of Abstract of JP2003-287882A, Oct. 10, 2003.
Machine English Translation of Abstract of P2003-238682A, Aug. 7, 2003.
Machine English Translation of Abstract of P2008-88368A, Apr. 14, 2008.
Machine English Translation of Abstract of JP2010-260883A, Nov. 18, 2010.
Machine English Translation of Abstract of JP2011-18778A, Jan. 27, 2011.
Craig J. Hawker et al., "Initiating Systems for Nitroxide-Mediated "Living" Free Radical Polymerizations: Synthesis and Evaluation", Macromolecules Vo. 29 No. 16, pp. 5245-pp. 5254 (1996) **Reference cited in previously submitted IDS, however, omitted to upload reference.
Iain E. Dunlop, "Interactions Between Polymer Brushes: Varying the Number of End-Attaching Groups", Macromol. Chem. Phys. vol. 205, pp. 2443-pp. 2450 (2004). **Reference cited in previously submitted IDS, however, omitted to upload reference.
Machine English Translation of Abstract of WO2012/161106A1, Nov. 29, 2012.

* cited by examiner

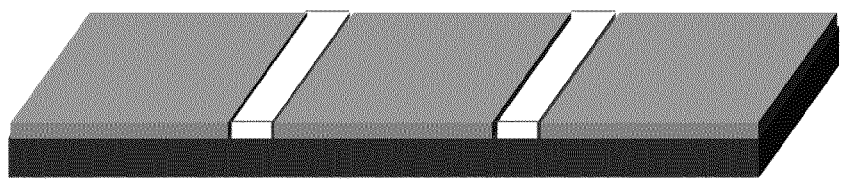
Fig 1 a
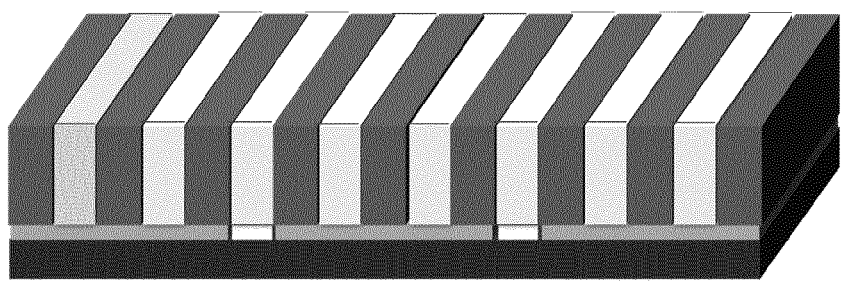
Fig 1 b
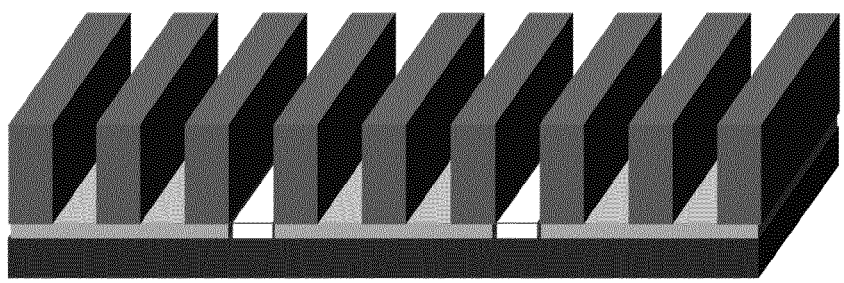
Fig 1 c
FIG. 1a-1c

POLYMER COMPOSITIONS FOR SELF-ASSEMBLY APPLICATIONS

This application is a United States National Stage Patent Application under 35 U.S.C. § 371 of International Patent Application No. PCT/EP2017/070726, filed Aug. 16, 2017 which claims priority to U.S. Provisional Patent Application No. 62/376,793, filed Aug. 18, 2016 the contents of each of which are being hereby incorporated herein by reference.

FIELD OF THE INVENTION

The invention relates to novel directing layer compositions which can act either as a neutral layer or a pinning layer and novel methods for using the neutral layer or pinning layer compositions for aligning microdomains of directed self-assembling block copolymers (BCP). The compositions and processes are useful for fabrication of electronic devices.

DESCRIPTION OF THE INVENTION

Directed self-assembly of block copolymers is a method useful for generating smaller and smaller patterned features for the manufacture of microelectronic devices in which the critical dimensions (CD) of features on the order of nanoscale can be achieved. Directed self-assembly methods are desirable for extending the resolution capabilities of microlithographic technology. In a conventional lithography approach, ultraviolet (UV) radiation may be used to expose through a mask onto a photoresist layer coated on a substrate or layered substrate. Positive or negative photoresists are useful and these can also contain a refractory element such as silicon to enable dry development with conventional integrated circuit (IC) plasma processing. In a positive photoresist, UV radiation transmitted through a mask causes a photochemical reaction in the photoresist such that the exposed regions are removed with a developer solution or by conventional IC plasma processing. Conversely, in negative photoresists, UV radiation transmitted through a mask causes the regions exposed to radiation to become less removable with a developer solution or by conventional IC plasma processing. An integrated circuit feature, such as a gate, via or interconnect, is then etched into the substrate or layered substrate, and the remaining photoresist is removed. When using conventional lithographic exposure processes, the dimensions of features of the integrated circuit feature are limited. Further reduction in pattern dimensions are difficult to achieve with radiation exposure due to limitations related to aberrations, focus, proximity effects, minimum achievable exposure wavelengths and maximum achievable numerical apertures. The need for large-scale integration has led to a continued shrinking of the circuit dimensions and features in the devices. In the past, the final resolution of the features has been dependent upon the wavelength of light used to expose the photoresist, which has its own limitations. Direct assembly techniques, such as graphoepitaxy and chemoepitaxy using block copolymer imaging, are highly desirable techniques used to enhance resolution while reducing CD variation. These techniques can be employed to either enhance conventional UV lithographic techniques or to enable even higher resolution and CD control in approaches employing EUV, e-beam, deep UV or immersion lithography. The directed self-assembly block copolymer comprises a block of etch resistant copolymeric unit and a block of highly etchable copolymeric unit, which when coated, aligned and etched on a substrate give regions of very high density patterns.

In the graphoepitaxy directed self-assembly method, the block copolymers self organizes around a substrate that is pre-patterned with conventional lithography (Ultraviolet, Deep UV, e-beam, Extreme UV (EUV) exposure source) to form repeating topographical features such as a line/space (LIS) or contact hole (CH) pattern. In an example of a LIS directed self-assembly array, the block copolymer can form self-aligned lamellar regions which can form parallel line-space patterns of different pitches in the trenches between pre-patterned lines, thus enhancing pattern resolution by subdividing the space in the trench between the topographical lines into finer patterns. For example, a diblock copolymer which is capable of microphase separation and comprises a block rich in carbon (such as styrene or containing some other element like Si, Ge, Ti) which is resistant to plasma etch, and a block which is highly plasma etchable or removable, can provide a high resolution pattern definition. Examples of highly etchable blocks can comprise monomers which are rich in oxygen and which do not contain refractory elements, and are capable of forming blocks which are highly etchable, such as methyl methacrylate. The plasma etch gases used in the etching process of defining the self-assembly pattern typically are those used in processes employed to make integrated circuits (IC). In this manner very fine patterns can be created in typical IC substrates than were definable by conventional lithographic techniques, thus achieving pattern multiplication. Similarly, features such as contact holes can be made denser by using graphoepitaxy in which a suitable block copolymer arranges itself by directed self-assembly around an array of contact holes or posts defined by conventional lithography, thus forming a denser array of regions of etchable and etch resistant domains which when etched give rise to a denser array of contact holes. Consequently, graphoepitaxy has the potential to offer both pattern rectification and pattern multiplication.

In chemical epitaxy or pinning chemical epitaxy the self-assembly of the block copolymer is formed around a surface that has regions of differing chemical affinity but no or very slight topography to guide the self-assembly process. For example, the surface of a substrate could be patterned with conventional lithography (UV, Deep UV, e-beam EUV) to create surfaces of different chemical affinity in a line and space (L/S) pattern in which exposed areas whose surface chemistry had been modified by irradiation alternate with areas which are unexposed and show no chemical change. These areas present no topographical difference, but do present a surface chemical difference or pinning to direct self-assembly of block copolymer segments. Specifically, the directed self-assembly of a block copolymer whose block segments contain etch resistant (such as styrene repeat unit) and rapidly etching repeat units (such as methyl methacrylate repeat units) would allow precise placement of etch resistant block segments and highly etchable block segments over the pattern. This technique allows for the precise placement of these block copolymers and the subsequent pattern transfer of the pattern into a substrate after plasma or wet etch processing. Chemical epitaxy has the advantage that it can be fined tuned by changes in the chemical differences to help improve line-edge roughness and CD control, thus allowing for pattern rectification. Other types of patterns such as repeating contact holes (CH) arrays could also be pattern rectified using chemoepitaxy.

Neutral layers are layers on a substrate or the surface of a treated substrate which have no affinity for either of the block segment of a block copolymer employed in directed self-assembly. In the graphoepitaxy method of directed self-assembly of block copolymer, neutral layers are useful as they allow the proper placement or orientation of block polymer segments for directed self-assembly which leads to proper placement of etch resistant block polymer segments and highly etchable block polymer segments relative to the substrate. For instance, in surfaces containing line and space features which have been defined by conventional radiation lithography, a neutral layer allows block segments to be oriented so that the block segments are oriented perpendicular to the surface of the substrates, an orientation which is ideal for both pattern rectification and pattern multiplication depending on the length of the block segments in the block copolymer as related to the length between the lines defined by conventional lithography. If a substrate interacts too strongly with one of the block segments it would cause it to lie flat on that surface to maximize the surface of contact between the segment and the substrate; such a surface would perturb the desirable perpendicular alignment which can be used to either achieve pattern rectification or pattern multiplication based on features created through conventional lithography. Modification of selected small areas or pinning of substrate to make them strongly interactive with one block of the block copolymer and leaving the remainder of the surface coated with the neutral layer can be useful for forcing the alignment of the domains of the block copolymer in a desired direction, and this is the basis for the pinned chemoepitaxy or graphoepitaxy employed for pattern multiplication.

There is a need for a novel materials which can form a crosslinked neutral copolymer layer or crosslinked pinning layer on a semiconductor (e.g. Si, GaAs, and the like), metal (Cu, W, Mo, Al, Zr, Ti, Hf, Au and the like) and metal oxide (Copper oxide, Aluminum oxide, Hafnium oxide, Zirconium oxide, Titanium oxide and the like) substrates through a simple spin coating, followed by a post coat bake to affect crosslinking of the layer.

The novel compositions comprise at least one random copolymer having at least one repeat unit of structure (1), which can be coated and subsequently crosslinked on a substrate to generate either a pinning layer or a neutral layer. In the case of the pinning layer it may be coated on a surface and subsequently patterned. The pinning patterned areas may be generated by patterning a coating of the novel pinning layer by coating the layer with an overlying patterned resist using the resist as a template to selectively etch the areas not protected by overlying resist with either a wet or dry chemical etch process. Alternatively, the patterned pinning may be obtained by coating a novel compositions tuned on a patterned substrate with a thickness just filling the voids in the pattern but not covering the top of the features. These layers formed from these composition may be used as directing layer (either as neutral or pinning layer) in self-assembly and directed self-assembly processes. These novel compositions which produce upon coating and crosslinking either neutral layer retain their original neutral or pinning behavior with respect to the self-assembly of block copolymer coated over these layer and are not damaged by processing steps employed in directed self-assembly techniques. Further they enhance the lithographic performance of the directed self-assembly materials and processes, especially reducing the number of processing steps and provide better pattern resolution with good lithographic performance. More specifically, in one embodiment, the present invention relates to novel compositions capable of forming a cross-linked layer upon heating coatings of these on a substrate at a temperature between about 200 and 350° C. which are insoluble in both organic solvents and aqueous bases where composition comprises at least one random copolymer having at least one repeat unit derived from an acrylate or methacrylate repeat unit with a pendant benzocyclobutene.

DETAILED DESCRIPTION OF DRAWINGS

FIG. 1a-1c show a self-alignment process.

FIG. 3a-3g show a process for positive tone multiplication.

SUMMARY OF INVENTION

Figures 2A, 2B, 2C, 2D, 2E, 2F, 2G, 2H, 2I:
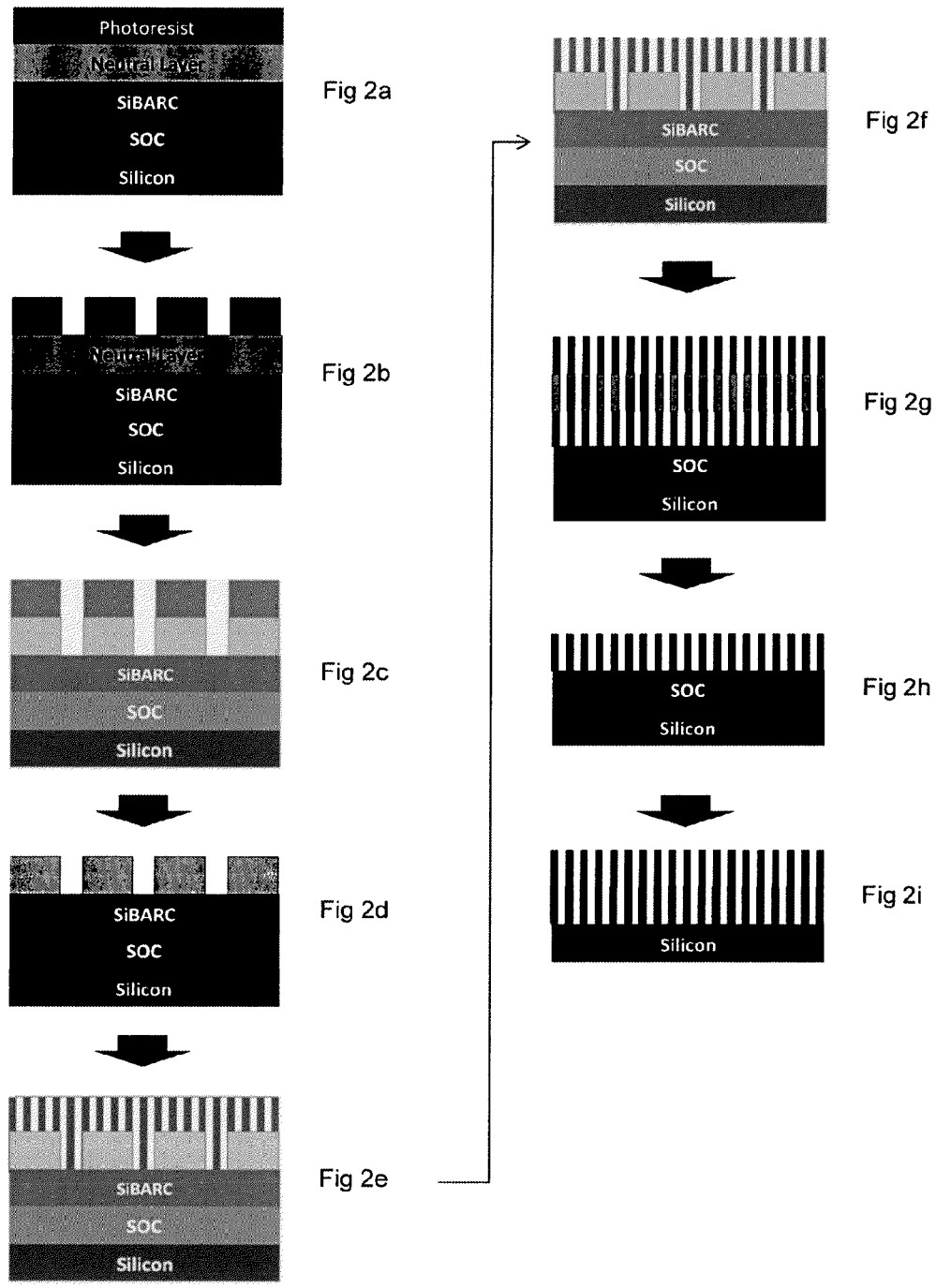
FIG. 2a-2i show a process for negative tone line multiplication.

The present invention relates to a composition comprising at least one random copolymer having at least one repeat unit of structure (1),

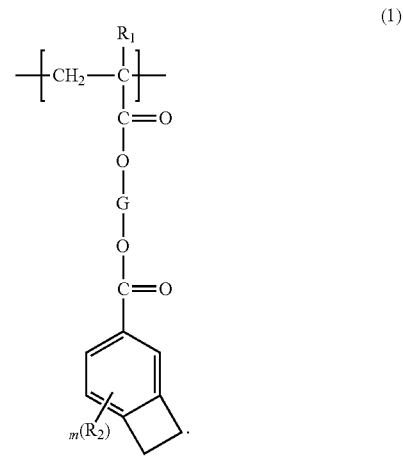

The present invention also relates to novel processes for forming patterns using this novel crosslinked layer on a substrate by enable a film of a block copolymer coated on the novel crosslinked layer to undergo self-aligned.

DETAILED DESCRIPTION OF THE INVENTION

Herein, alkyl refers to saturated hydrocarbon groups which can be linear or branched (e.g. methyl, ethyl, propyl, isopropyl, tert-butyl and the like), cycloalkyl refers to a hydrocarbon containing one saturated cycle (e.g. cyclohexyl, cyclopropyl, cyclopentyl and the like), fluoroalkyl refers to a linear or branched saturated alkyl group in which all (a.k.a. fully fluorinated) or part (a.k.a. partially fluorinated) of the hydrogens have been replaced by fluorine, cyclofluoroalkyl refers to a cycloalkyl group in which all (a.k.a. fully fluorinated) or part of (a.k.a. partially fluorinated) the hydrogens have been replaced by fluorine; hydroalkyl refers to an alkyl or cycloalkyl group which is substituted with a least one hydroxyl moiety (e.g. —CH$_2$—CH$_2$—OH, CH—CH(OH)—CH$_3$ and the like). The term ethylenic monomer refers to a moiety containing a carbon-carbon double bond which can undergo a polymerization reaction to form a polymer repeat unit. Non-limiting examples of such monomers are derivatives of styrene, alkyl methacrylates, alkyl acrylates and the like. When designating in the following text any of the above alkyl moiety or alkyl containing moieties with a further limitation with regards to the number of carbons, for instance, as a non-limiting examples, C-1 to C-10; this further limitation comes the further implied limitation that only linear alkyl may have just one or two carbon, that branched or cyclic alkyls must have at least 3 carbons. Also, it is further defined herein that cyclic moieties containing 5 and/or 6 carbon or containing at least 5 and/or 6 carbons are possible preferred embodiments. The term "(meth)acrylate" is a moiety which embodies both the term "acrylate" and "methacrylate." When discussing the random polymers of this application containing repeat units (1), (2) or (3), the term "copolymer" is employed for all these polymers even in the case when only repeat unit (1) is present in a given polymer under discussion. The term "chemoepitaxy is synonymous with "chemical epitaxy."

The present invention relates to novel neutral layer and novel pinning layer compositions and novel self-directed assembly processes for forming patterns with high resolution and good lithographic properties using these novel compositions. These novel compositions, depending the exact repeat unit composition of the random copolymer containing at least one repeat unit (1), are capable of either forming, upon coating and crosslinking on a substrate a neutral layer region or a pinning layer region for use with self-assembly of block copolymers. The neutral layer is an orientation control layer which allows the block copolymer coated above the neutral layer to align in the desirable direction relative to the substrate for where the block copolymer domains are oriented in a direction perpendicular to the substrate for high resolution lithography application. pinning layer regions also affect the orientation of block polymer domains on a substrate; but, in this instance, the pinning layer regions show a preference for one of the block copolymer domains making it align parallel to the pinning layer region. The invention also relates to novel processes for use in directed self-assembly of block copolymers, such as graphoepitaxy and chemoepitaxy, which use crosslinked layer regions of the novel compositions as either neutral layer or pinning layer regions.

As a general guide, unless defined more specified elsewhere herein, the novel directing layers are pinning layers in which the crosslinked random monomer composition of the layer tends to resemble one of the block copolymer domains overlying the pinning layer. This resemblance may be one where the repeat units that randomly predominate in the pinning layer composition resembles in terms of composition and/or polarity one of the block copolymers domains. For instance, a directing layer where styrenic like repeat units randomly predominates will tend to act as a pinning layer for styrenic like domains of an overlying block copolymer during directed self-assembly. Conversely, a directing layer where (meth)acrylate like repeat in random fashion predominate will act as a pinning layer for (meth)acrylate like domains of a overlying block copolymer.

In one embodiment of these novel compositions for pinning application, a polymer comprises of at least one repeat unit of structure (1) but also has a composition in which one type of repeat unit in the pinning layer is present in equal or greater amount than about 60 mole %. When this polymer is coated on a substrate and crosslinked the predomination of this one type of repeat unit will produce a pinning layer which has an affinity a to block copolymer domains which has a similar polarity when such a block copolymer is coated over the pinning layer and undergoes self-assembly. In another embodiment of this aspect of the invention, the predomination is greater than about 70 mole %, in yet another embodiment it is greater than about 80 mole %, in yet another embodiment it is greater than about 90 mole %. For instance, in a non-limiting examples the predominance of (meth)acrylate like repeat unit (1) alone or combination with the (meth)acrylate like unit (2) will lead to a composition will act as pinning layer towards (meth) acrylate like block copolymer domains. Conversely, in the novel compositions containing a polymer having ate least one repeat of structure (1), the predominance of styrenic like repeat units (3) over (meth)acrylic like repeat units (1) alone or combination with (meth)acrylic like repeat unit (2) will lead to a directing layer which will be pinning towards styrenic like block copolymer domains. However, in no instance may a composition have a total mole % composition of repeat units exceeding 100 mole %.

Similarly, a polymer which comprises at least one repeat unit of structure (1), but in which the (meth)acrylate like repeat units (1) alone or combination (2) do not predominate over styrenic like repeat units (3) will yield upon coating on a substrate and crosslinking a neutral layer towards a overlying block copolymer film in which the block copolymer has block copolymer domains of polarity similar to (1) and/or (2) and blocks polymer domains of polarity similar to the styrenic repeat units (3). For instance, in a non-limiting example, novel directing layers will act as neutral layers towards the domains of a block copolymer of styrene like and meth(acrylate) like if the random composition of units of corresponding polarity in the directing layer is about 50 mole % to about 55 mole % each of styrene like and meth(acrylate) repeat units. In another embodiment, the composition of styrene is about 50 mole %. In no instance may a random copolymer employed to make a neutral layer have a composition have a mole % composition of repeat units exceeding 100 mole %.

The invention leads to further improvement in resolution or CD uniformity of targeted features made by conventional lithographic techniques, such as UV lithography (450 nm to 10 nm), immersion lithography, EUV or e-beam.

In one aspect of this invention the novel composition comprises at least one random copolymer having at least one repeat unit of structure (1),

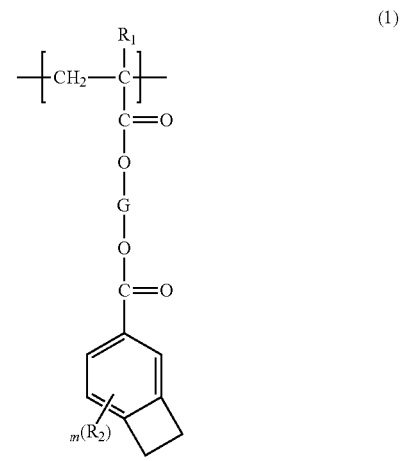

where $R_1$ is selected from a group consisting of H, C-1 to C-4 alkyl, a C-1 to C-4 fluoroalkyl, and a halide; and $R_2$ is selected from the group consisting of H, F, C-1 to C8 alkyl and a C-1 to C-8 fluoroalkyl and m ranges from 1 to 3 and G is a C-2 to C-10 alkylene moiety.

In another aspect of this embodiment in structure (1), $R_1$ is selected from the group consisting of H, and a C-1 to C-4 alkyl.

In another embodiment in structure (1), $R_1$ is a C-1 to C-4 alkyl.

In another embodiment in structure (1), $R_1$ is H.

More specifically in another aspect of the above composition, the novel composition is one, which upon coating, on a substrate, is capable of forming a cross-linked layer on the substrate upon heating at a temperature between about 220 and about 300° C. This crosslinked layer is insoluble in both organic solvents and aqueous bases and capable of affecting self-assembly of the block domains of a block copolymer cast on top of it and annealed.

In another embodiment in structure (1), $R_1$ is methyl. In another embodiment in structure (1), G is a C-2 to C-5 alkylene moiety. In another embodiment in structure (1),), G is ethylene. In another embodiment in structure (1), m is 3, and $R_2$ is methyl.

The term random copolymer as used above not only designates copolymers containing repeat units of structures (1) and other chemically distinct repeat units derived from ethylenic monomers, but also embodies random copolymers with repeat units of structure (1) having different substituents, and also homopolymers consisting only of repeat units having structure (1) with the same substituents.

The novel random copolymers containing at least one repeat unit of structure (1) of this invention, described herein, inherently have end groups. As non-limiting examples, if the novel random copolymer is produced through a standard radical initiator (e.g. AIBN, peroxide initiators and the like), these end groups will be derived from these standard radical initiators as shown as non-limiting examples in structures 1' and 1":

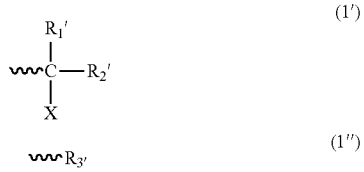

where $R_{1'}$ and $R_{1''}$ are independently a C-1 to C-8 alkyl and X is —CN, or an alkyloxycarbonyl moiety $R_{4'}$—O—(C=O)— where $R_{4'}$ is a C-1 to C-8 alkyl; $R_{3'}$ is H, a C-1 to C-8 alkyl, an alkoxyalkyl alkylcarbonyloxy (—O—C=O—$R_{4'}$), arylcarbonyloxy (—O—C=O-aryl), an aryl moiety; and ⁓ represent the attachment point of the end group to the novel random copolymer of this invention.

Additionally, another non-limiting examples of possible end groups for the novel random copolymers of this invention is when the end group is ones which contain a functional group which allow grafting of the novel random copolymers of this invention onto a substrate such as shown in non-limiting example structure (1'");

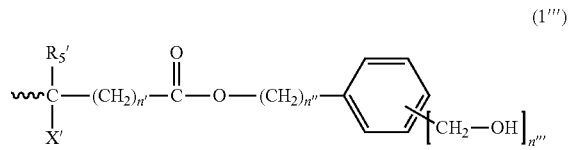

where $R_{5'}$ is a C-1 to C-8 alkyl and X is —CN, or an alkyloxycarbonyl moiety $R_{6'}$—O—(C=O)— where $R_{6'}$ is a C-1 to C-8 alkyl and ⁓ represent the attachment point of the end group to the random copolymer of this invention. Such grafting end groups are discussed in U.S. patent application Ser. No. 14/885,328 which is incorporated by reference which pertains to crosslinking polymer which contain a repeat unit with a pendant benzocyclobutene to a styrenic derived repeat moiety in the polymer which acts as a crosslinking site and also contains an end group as shown in structure (1'") which act as a grafting moiety.

In another embodiment of this novel composition the random copolymer having at least one repeat unit of structure (1), is one wherein $R_1$ is selected from a group consisting of H, methyl, and $R_2$ is H and G is a C-2 to C-5 alkylene moiety.

In another embodiment of this novel composition the random copolymer having at least one repeat unit of structure (1), is one which further comprises at least one repeat units of structure (2) and at least one repeat unit of structure (3),

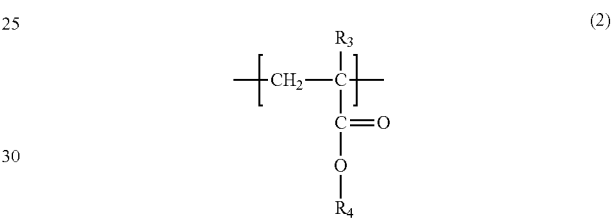

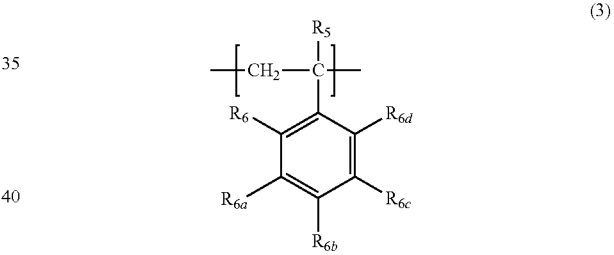

where $R_3$ is hydrogen, a C-1 to C-4 fluoroalkyl or a C-1 to C-4 alkyl, $R_4$ is a C-1 to C-20 alkyl, a halide, a C-1 to C-10 fluoroalkyl group, or a (trialkylsilyl)alkylene group, $R_5$ is hydrogen, a C-1 to C-4 alkyl, or a C-1 to C-4 fluoroalkyl, $R_6$, $R_{6a}$, $R_{6b}$, $R_{6c}$ and $R_{6d}$ are independently selected from the group consisting of hydrogen, a C-1 to C-20 alkyl, a C-1 to C-20 alkoxy, a C-1 to C-10 fluoroalkyl, a C-1 to C-10 fluoroalkoxy, a trialkylsilyl group, a (trialkylsilyl)alkylene group, and a (trialkylsilyl)alkyleneoxy group.

In another embodiment in structure (2), $R_3$ is H or a C-1 to C-4 alkyl. In still another embodiment $R_3$ is H. In still another embodiment $R_3$ is a C-1 to C-4 alkyl. In another further embodiment $R_3$ is methyl.

In another embodiment in structure (2), R4 is a C-1 to C-4 alkyl. In another further embodiment $R_4$ is methyl.

In another embodiment in structure (3), $R_5$ is hydrogen or a methyl. In still another embodiment $R_5$ is hydrogen.

In another embodiment in structure (3), $R_6$, $R_{6a}$, $R_{6b}$, $R_{6c}$ and $R_{6d}$ are independently selected from hydrogen or a C-1 to C-10 alkyl. In still another embodiment $R_6$, $R_{6a}$, $R_{6b}$, $R_{6c}$ and $R_{6d}$ are independently selected from hydrogen or a C-1 to C-4 alkyl. In still another embodiment $R_6$, $R_{6a}$, $R_{6b}$, $R_{6c}$ and $R_{6d}$ are all selected from hydrogen.

In another embodiment of this novel composition the random copolymer having at least one repeat unit of structure (1), is one in which said random copolymer further comprises at least one repeat unit having structure (2),

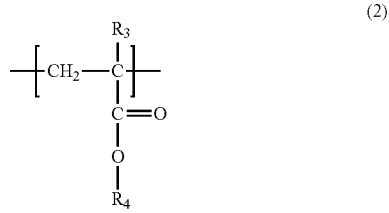
(2)

where $R_3$ is hydrogen, a C-1 to C-4 fluoroalkyl or a C-1 to C-4 alkyl, $R_4$ is a C-1 to C-20 alkyl, a C-1 to C-10 fluoroalkyl group, or a (trialkylsilyl)alkylene group. In another embodiment of this aspect of the invention in structure (2), $R_3$ is H or a C-1 to C-4 alkyl. In still another embodiment $R_3$ is H. In still another embodiment $R_3$ is a C-1 to C-4 alkyl. In another further embodiment $R_3$ is methyl. In another embodiment, in structure (2), $R_4$ is a C-1 to C-4 alkyl. In another further embodiment $R_4$ is methyl.

In another embodiment of this novel composition, the random copolymer having at least one repeat unit of structure (1), is one wherein said random copolymer further comprises at least one styrenic repeat having structure (3),

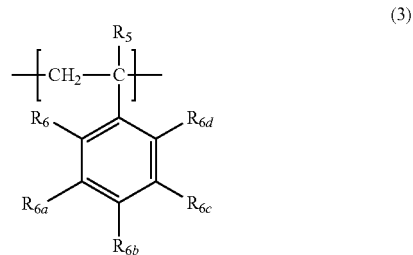
(3)

where $R_5$ is hydrogen, a C-1 to C-4 alkyl, or a C-1 to C-4 fluoroalkyl, $R_6$, $R_{6a}$, $R_{6b}$, $R_{6c}$ and $R_{6d}$ are independently selected from the group consisting of hydrogen, a C-1 to C-20 alkyl, a C-1 to C-20 alkoxy, a C-1 to C-10 fluoroalkyl, a C-1 to C-10 fluoroalkoxy, a trialkylsilyl group, a (trialkylsilyl)alkylene group, and a (trialkylsilyl)alkyleneoxy group. A more specific embodiment of this is where $R_1$ is selected from a group consisting of H, methyl, and $R_2$ is H and G is a C-2 to C-5 alkylene moiety, and further where $R_5$ is hydrogen, $R_6$, $R_{6a}$, $R_{6b}$, $R_{6c}$, and $R_{6d}$ are independently hydrogen, a C-1 to C-4 alkyl, or a C-1 to C-4 alkoxy. In aspect of this invention in structure (3), $R_5$ is hydrogen or a methyl. In still another embodiment $R_5$ is hydrogen. In another embodiment in structure (3), $R_6$, $R_{6a}$, $R_{6b}$, $R_{6c}$ and $R_{6d}$ are independently selected from hydrogen or a C-1 to C-10 alkyl. In still another embodiment $R_6$, $R_{6a}$, $R_{6b}$, $R_{6c}$ and $R_{6d}$ are independently selected from hydrogen or a C-1 to C-4 alkyl. In still another embodiment $R_6$, $R_{6a}$, $R_{6b}$, $R_{6c}$ and $R_{6d}$ are all selected from hydrogen.

In another embodiment of this novel composition, the random copolymer having at least one repeat unit of structure (1), when coated on a substrate and crosslinked, is a directing layer which act as a pinning layer for a block copolymer film cast on top of it where the block copolymer is comprised of a block of polar aliphatic monomeric repeat units with a high etch rate and a block of monomeric aromatic units with low etch rate in a plasma comprising oxygen and where the directing layer polymer acts as a pinning layer, during self-assembly of the block copolymer domains in the film, for the block copolymer's domains comprised of polar aliphatic monomeric repeat units. In a more specific embodiment of this aspect of the invention $R_1$ is H or methyl, $R_2$ is H and G is a C-2 to C-5 alkylene moiety. In yet another embodiment $R_1$ is H, in another $R_1$ is methyl, in another $R_2$ is H, in another G is a C-2 alkylene, in another G is a C-3 alkylene, in another G is a C-4 alkylene, in yet another G is a C-5 alkylene.

In another embodiment of this novel composition the random copolymer having at least one repeat unit of structure (1), is one where said random copolymer comprised of repeat unit of structure (1), and repeat units of structure (2) as described above. When this polymer coated on a substrate and crosslinked, is a directing layer which act as a pinning layer for a block copolymer film cast on top of it where the block copolymer is comprised of a block of polar aliphatic repeat units having an acrylate like structure (2a) with a high etch rate and a block of an aromatic units having a styrenic like structure (3a) with low etch rate in a plasma comprising oxygen and where the directing layer polymer acts as a pinning layer with an affinity for the polymer block domains of overlying block copolymer film derived from (meth) acrylate repeat units during self-assembly of the block copolymer domains in the film,

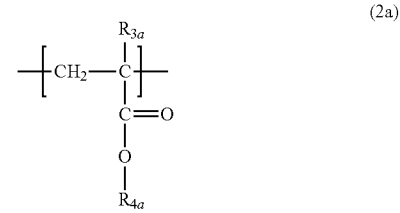
(2a)

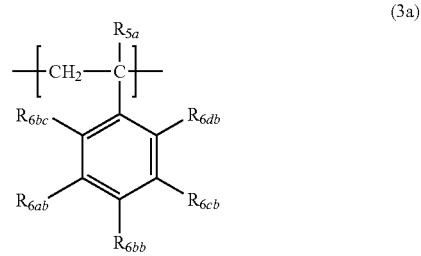
(3a)

where $R_3$ and $R_{3a}$ are independently selected from hydrogen, a C-1 to C-4 fluoroalkyl or a C-1 to C-4 alkyl, $R_4$ and $R_{4a}$ are independently selected a C-1 to C-20 alkyl, a halide, a C-1 to C-10 fluoroalkyl group, or a (trialkylsilyl)alkylene group, $R_{5a}$ is selected from hydrogen, a C-1 to C-4 alkyl, or a C-1 to C-4 fluoroalkyl, $R_{6ab}$, $R_{6bb}$, $R_{6cb}$, and $R_{6db}$, are independently selected from the group consisting of hydrogen, a C-1 to C-20 alkyl, a C-1 to C-20 alkoxy, a C-1 to C-10 fluoroalkyl, a C-1 to C-10 fluoroalkoxy, a trialkylsilyl group, a (trialkylsilyl)alkylene group, and a (trialkylsilyl)alkyleneoxy group where; $R_{3a}$ is hydrogen, a C-1 to C-4 fluoroalkyl, a halide, or a C-1 to C-4 alkyl, $R_{4a}$ is a C-1 to C-20 alkyl, or a C-1 to C-10 fluoroalkyl group. In a more specific aspect of this embodiment the random copolymer is one in which $R_1$ is H or methyl, $R_2$ is H and G is a C-2 to C-5 alkylene moiety $R_3$ is hydrogen, or a C-1 to C-4 alkyl, and $R_4$ is a C-1 to C-20 alkyl, or a C-1 to C-10 fluoroalkyl group. In another more specific embodiment of this aspect the block copolymer is one where $R_{3a}$ is hydrogen, or a C-1 to C-4 alkyl, and R4a is a C-1 to C-20 alkyl, or a C-1 to C-10 fluoroalkyl group and $R_{5a}$ hydrogen, $R_{6b}$, $R_{6ab}$, $R_{6bb}$, $R_{6cb}$, and $R6_{db}$, are independently selected from the group consisting of hydrogen, a C-1 to C-20 alkyl, a C-1 to C-10 fluoroalkyl. In another aspect of this embodiment of the invention in structure (2a) $R_{3a}$ is H or a C-1 to C-4 alkyl. In still another embodiment $R_{3a}$ is H. In still another embodiment $R_{3a}$ is a C-1 to C-4 alkyl. In another further embodiment $R_{3a}$ is methyl. In another embodiment in structure (2), R4a is a C-1 to C-4 alkyl. In another further embodiment $R_{4a}$ is methyl.

In another aspect of this invention in structure (3a), R5a is hydrogen or a methyl. In still another embodiment $R_{5a}$ is hydrogen. In another embodiment in structure (3a), $R_{6bc}$, $R_{6ab}$, $R_{6bb}$, $R_{6cb}$, and $R_{6db}$, are independently selected from hydrogen or a C-1 to C-10 alkyl. In still another embodiment R $R_{6bc}$, $R_{6ab}$, $R_{6bb}$, $R_{6cb}$, and $R_{6db}$ are independently selected from hydrogen or a C-1 to C-4 alkyl. In still another embodiment $R_{6bc}$, $R_{6ab}$, $R_{6bb}$, $R_{6cb}$, and $R_{6db}$ are all selected from hydrogen.

In another embodiment of this novel composition the random copolymer having at least one repeat unit of structure (1), is one where the random copolymer comprised of repeat unit of structure (1) and repeat units of structure (3), as described above, which when coated on a substrate and crosslinked, is a directing layer which act as a pinning layer for a block copolymer film cast on top of it where the block copolymer is comprised of a block of (meth)acrylate structure (2a) and a block of styrenic repeat units of structure (3a), as described above.

In another embodiment in structure (3), $R_6$, $R_{6a}$, $R_{6b}$, $R_{6c}$ and $R_{6d}$ are independently selected from hydrogen or a C-1 to C-10 alkyl. In still another embodiment $R_{6a}$, $R_{6b}$, $R_{6c}$ and $R_{6d}$ are independently selected from hydrogen or a C-1 to C-4 alkyl. In still another embodiment $R_6$, $R_{6a}$, $R_{6b}$, $R_{6c}$ and $R_{6d}$ are all selected from hydrogen. In another aspect of this embodiment of the invention in structure (2a) $R_{3a}$ is H or a C-1 to C-4 alkyl. In still another embodiment $R_{3a}$ is H. In still another embodiment $R_{3a}$ is a C-1 to C-4 alkyl. In another further embodiment $R_{3a}$ is methyl. In another embodiment in structure (2), $R_{4a}$ is a C-1 to C-4 alkyl. In another further embodiment $R_{4a}$ is methyl. In another aspect of this invention in structure (3a), $R_{5a}$ is hydrogen or a methyl. In still another embodiment $R_{5a}$ is hydrogen. In another embodiment in structure (3a), $R_{6bc}$, $R_{6ab}$, $R_{6bb}$, $R_{60}$, and $R_{6db}$, are independently selected from hydrogen or a C-1 to C-10 alkyl. In still another embodiment $R_{6bc}$, $R_{6ab}$, $R_{6bb}$, $R_{6cb}$, and $R_{6db}$ are independently selected from hydrogen or a C-1 to C-4 alkyl. In still another embodiment $R_{6bc}$, $R_{6ab}$, $R_{6bb}$, $R_{6cb}$, and $R_{6db}$ are all selected from hydrogen.

In another embodiment of this novel composition the random copolymer having at least one repeat unit of structure (1), is one where the random copolymer comprised repeat unit of structure (1) and repeat units of structures (2) and (3), as described above, which when coated on a substrate and crosslinked, is a directing layer which act as a neutral layer for a block copolymer film cast on top of it where the block copolymer is comprised of a block of polar aliphatic repeat units having (meth)acrylate like structure (2a) and a block of aromatic repeat units having styrenic like structure (3a), as described above.

Another embodiment of this invention is the novel monomer of structure (1''')

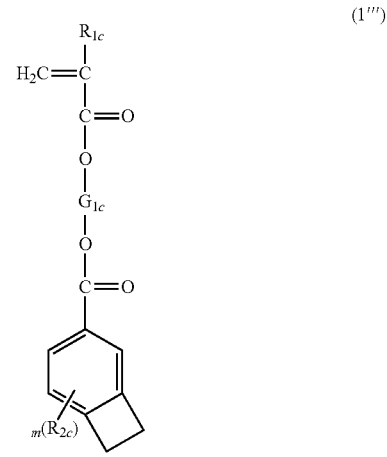

$R_{1c}$ is selected from a group consisting of H, C-1 to C-4 alkyl, a C-1 to C-4 fluoroalkyl, and a halide; and $R_{2c}$ is selected from the group consisting of H, F, C-1 to C-8 alkyl and a C-1 to C-8 fluoroalkyl and m ranges from 1 to 3 and $G_{1c}$ is a C-2 to C-10 alkylene moiety. Another aspect of this invention are novel random copolymers having at least one repeat unit of structure (1);

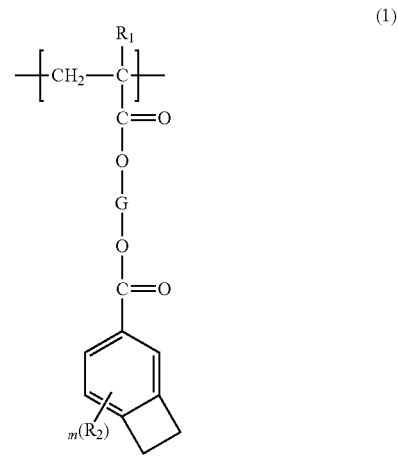

where $R_1$ is selected from a group consisting of H, C-1 to C-4 alkyl, a C-1 to C-4 fluoroalkyl, and a halide; and $R_2$ is selected from the group consisting of H, F, C-1 to C-8 alkyl and a C-1 to C-8 fluoroalkyl and m ranges from 1 to 3 and G is a C-2 to C-10 alkylene moiety. Other aspects of this novel random copolymer are described above in the descriptions of the novel compositions in which these differing aspect of this novel polymer as described when it was described as a component in the novel compositions.

The novel random polymer containing at least one novel repeat unit (1) can be prepared by using a diazo initiator to prepare from the corresponding monomers (structure (1)). Specifically, a polymer in which only one type repeat unit of structure (1) is present, a polymer in which a mixture of different types of repeat unit of structure (1) can be prepared from the corresponding monomer having structure (1').

Similarly, polymers can be prepared which contain mixture of repeat unit (1) with repeat unit (2), mixture of repeat unit having structure (1) with repeat unit having structure (3), or mixtures of repeat unit having structure (1) with ones having structures (2) and (3) from the corresponding monomers having structures (2') and (3'). Such polymers containing repeat units (2) and/or (3) may have these present as one type of each of these repeat units or ones which have differing substitution by appropriate selection of monomers.

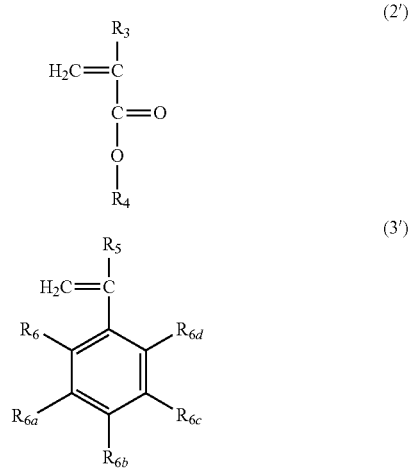

In structures (2') and (3') where $R_3$ is hydrogen, a C-1 to C-4 fluoroalkyl or a C-1 to C-4 alkyl, $R_4$ is a C-1 to C-20 alkyl, a halide, a C-1 to C-10 fluoroalkyl group, or a (trialkylsilyl)alkylene group, $R_5$ is hydrogen, a C-1 to C-4 alkyl, or a C-1 to C-4 fluoroalkyl, $R_6$, $R_{6a}$, $R_{6b}$, $R_{6c}$ and $R_{6d}$ are independently selected from the group consisting of hydrogen, a C-1 to C-20 alkyl, a C-1 to C-20 alkoxy, a C-1 to C-10 fluoroalkyl, a C-1 to C-10 fluoroalkoxy, a trialkylsilyl group, a (trialkylsilyl)alkylene group, and a (trialkylsilyl)alkyleneoxy group. In another embodiment of this aspect of the invention in structure (2'), $R_3$ is H or a C-1 to C-4 alkyl. In still another embodiment $R_3$ is H. In still another embodiment $R_3$ is a C-1 to C-4 alkyl. In another further embodiment $R_3$ is methyl. In another embodiment in structure (2'), R4 is a C-1 to C-4 alkyl. In another further embodiment $R_4$ is methyl. In another embodiment in structure (3'), $R_6$, $R_{6a}$, $R_{6b}$, $R_{6c}$ and $R_{6d}$ are independently selected from hydrogen or a C-1 to C-10 alkyl. In still another embodiment $R_6$, $R_{6a}$, $R_{6b}$, $R_{6c}$ and $R_{6d}$ are independently selected from hydrogen or a C-1 to C-4 alkyl. In still another embodiment $R_6$, $R_{6a}$, $R_{6b}$, $R_{6c}$ and $R_{6d}$ are all selected from hydrogen.

In the novel compositions comprised of a random copolymer comprised of repeat units of structures (1), (2) and (3), as described above, the repeat unit (1) may range from about 5 mole % to about 60 mole %; unit (2) ranges from about 10 mole % to about 60 mole % and unit 3 ranges from about 10 mole % to about 60 mole %. In another embodiment of this aspect of the invention unit (1) may range from about 10 mole % to about 30 mole %; unit (2) ranges from about 20 mole % to about 50 mole % and unit 3 ranges from about 20 mole % to about 40 mole %. In another embodiment repeat unit (1) may range from about 5 mole % to about 60 mole %. In another unit (2) may range from about 10 mole % to about 60 mole %. In another embodiment unit 3 ranges from about 10 mole % to about 60 mole %. In another embodiment unit (1) may range from about 10 mole % to about 30 mole %. In another embodiment unit (2) about 20 mole % to about 50 mole %. In another embodiment and unit 3 may from about 20 mole % to about 40 mole %. In aspects of this invention when this embodiment of the composition is coated on a substrate as a layer and is engineered to be a neutral directing layer when crosslinked towards an overlying block copolymer coating containing (meth)acrylate like block domains and styrene like block domains derived from the corresponding repeat units (i.e. (2a) and (3a) respectively), it is preferred that the total composition of the polar (meth)acrylate unit (1) and unit (2) together may range from about 55 to about 45 mole % and that the corresponding composition of unit styrenic unit 3 may range from about 55 to about 55 mole %, or more preferentially where both types of unit are about 50 mole %. In embodiments where the composition when coated on a subtracted and crosslinked would act as a pinning directing layer towards (meth)acrylate like polymer block domains it is preferred that the total composition of the polar (meth)acrylate unit (1) and unit (2) together may range from about 60 to about 99 mole %, or alternatively about 65 mole %, about 70 mole %, or about 75 mole %, or about 80 mole %, or about 85 mole %, or about 90 mole % or about 95 mole %. The corresponding composition of styrenic like units (3) may range from about 30 to about 1 mole %, or alternatively about 25 mole %, or about 20 mole % or about 15 mole % or about 10 mole %. In another embodiment of this aspect of this invention where the composition when coated on a subtracted and cross-linked would act as a pinning directing layer towards styrenic like polymer block domains, it is preferred that the total composition of the polar (meth)acrylate unit (1) and unit (2) together may range from about 55 to about 5 mole %, in another embodiment this total is about 55 mole %, in another about 50 mole %, in another about 45 mole %, in another about 40 mole %, in another about 35 mole %, in another about 30 mole %, in another about 25 mole %, in another about 20 mole %, in another about 15 mole %, in another about 10 mole %, and in yet another about 5 mole %. In this pinning layer embodiment the corresponding composition of styrenic like units (3) may range from about 95 mole % to about 60 mole %, or in another embodiment may be about 60 mole %, or about 65 mole %, or about 70 mole %, or about 75 mole % or about 80 mole % or about 85 mole % or about 90 mole % or about 95 mole %. In any of the above aspect of this invention the total mole % composition of repeat units in random copolymer may not exceed 100 mole %.

In the novel compositions comprised of a random copolymer comprised of repeat units of structures (1), and (2) repeat described above unit (1) may range from about 5 mole % to about 50 mole %; and unit (2) may range from about 10 mole % to about 95 mole %. In another embodiment of this aspect of the invention unit (1) may range from about 10 mole % to about 30 mole %; and unit (2) may range from about 20 mole % to about 80 mole %. %. In another embodiment, unit (1) may range from about 5 mole to about 50 mole %. In another embodiment unit (2) may range from about 10 mole % to about 95 mole %. In another embodiment unit (1) may range from about 10 mole % to about 30 mole %. In another embodiment unit (2) may range from about 20 mole % to about 80 mole %. %. In another aspect of this aspect of the invention when this embodiment of the composition is coated on a substrate as a layer, and crosslinked, and is engineered to be a pinning directing layer towards (meth)acrylate like block domains during self-assembly of an overlying coating of a block a block copolymer containing (meth)acrylate like block domains and styrene like block domains derived from the corresponding repeat units (i.e. (2a) and (3a) respectively), it is preferred that the total composition of the polar (meth)acrylate unit (1) and (2) may range from about 60 to about 95 mole %, in another embodiment this total is about 65 mole %, in another about 70 mole %, in another about 75 mole % in another about 80 mole %, in another about 85 mole %, in another about 90 mole %, and yet another about 95 mole %.

In embodiments where the crosslinked directing layer is designed to function as a pinning layer towards styrenic like block copolymer domains, it is preferred that unit (1) in the novel copolymer may range in composition between about 5 and about 45 mole %, in another aspect of this embodiment about 5 mole %, or about 10 mole %, or about 15 mole %, or about 20 mole %, or about 25 mole %, or about 30 mole % or about 35 mole %, or about 40 mole %, or finally about 45 mole %; similarly, in this pinning aspect of the invention the composition of unit (2) may range between about 55 to about 95 mole %, or in another aspect of this embodiment about 55 mole %, or about 60 mole %, or about 65 mole %, or about 70 mole % or about 75 mole %, or about 80 mole %, or about 85 mole %, or about 90 mole % or finally about 95 mole %. In any of the above aspect of this invention the total composition in the random copolymer of repeat unit may not exceed 100 mole %.

In the novel compositions comprised of a random copolymer polymer comprised of repeat units of structures (1), and (3), described above, unit (1) may range from about 5 mole % to about 90 mole %; and unit 3 may range from about 10 mole % to about 90 mole % In another embodiment of this aspect of the invention unit (1) may range from about 10 mole % to about 80 mole %; and unit 3 may range from about 20 mole % to about 80 mole %. In another embodiment unit (1) may range from about 5 mole % to about 90 mole %. In another embodiment unit (1) may range from about 10 mole % to about 90 mole %. In another embodiment, unit 3 may range from about 10 mole % to about 90 mole %. In another embodiment unit 3 may range from about 20 mole % to about 80 mole %. In aspects of this invention when this embodiment of the composition is coated on a substrate as a layer and is engineered to be a neutral directing layer when crosslinked towards an overlying block copolymer coating containing (meth)acrylate like block domains and styrene like block domains derived from the corresponding repeat units (i.e. 2a and 3a respectively), it is preferred that the composition of the polar (meth) acrylate unit (1) may range from about 5 to about 90 mole %, or in another embodiment about 5 mole %, or about 10 mole % or about 15 mole % or about 20 mole % or about 25 mole % or about 30 mole % or about 35 mole % or about 40 mole % or about 45 mole %, or about 50 mole %, or about 55 mole %, or about 60 mole %, or about 65 mole %, or about 70 mole %, or about 75 mole %, or about 80 mole %, or about 85 mole %, or about 90 mole %. The corresponding composition of styrenic unit (3) may range from about 10 mole % to about 90 mole %, or in another aspect of this embodiment, or about 10 mole %, or about 15 mole %, or about 20 mole %, or about 25 mole %, or about 30 mole %, or about 35 mole %, or about 40 mole %, or about 45 mole %, or about 50 mole %, or about 55 mole %, or about 60 mole %, or about 65 mole %, or about 70 mole %, or about 75 mole %, or about 80 mole %, or about 85 mole %, or about 90 mole %. In embodiments where this composition when coated on a subtracted and crosslinked would act as a pinning directing layer towards (meth)acrylate like polymer block domains it is preferred that the composition of the polar (meth)acrylate unit (1) may range from about 60 to about 90 mole %, or about 60 mole %, or about 65 mole %, or about 70 mole %, or about 75 mole %, or about 80 mole %, or about 85 mole %, or finally about 90 mole %. Similarly, the corresponding composition of styrenic like units (3) in these polymers may range from about 40 to about 10 mole %, or about 10 mole %, or about 15 mole %, or about 20 mole %, or about 25 mole %, or about 30 mole %, or about 35 mole %, or finally about 40 mole %. In another embodiment, of this aspect of this invention where the composition when coated on a substrate and crosslinked would act as a pinning directing layer towards styrenic like polymer block domains, it is preferred that the composition of the polar (meth)acrylate unit (1) may range from about 40 mole % to about 5 mole %, or about 40 mole %, or about 35 mole %, or about 30 mole %, or about 25 mole %, or about 20 mole %, or about 15 mole %, or about 10 mole %, or about 5 mole %; and that similarly the corresponding composition of styrenic like units (3) may range from about 95 mole to about 60 mole %, or about 60 mole %, or about 65 mole %, or about 70 mole %, or about 75 mole %, or about 80 mole %, or about 85 mole %, or about 90 mole % or about 95 mole %. In another embodiment of this aspect of this invention where the composition when coated on a substrate and crosslinked would act as a neutral directing layer towards styrenic like polymer block domains, it is preference that the composition of the polar (meth)acrylate unit (1) may range from about 55 to about 45 mole % and that the corresponding composition of unit styrenic unit (3) may range from about 55 to about 55 mole %, or more preferentially where both types of unit are about 50 mole %. In any of the above aspect of this invention the total composition repeat units the random copolymer may not exceed 100 mole %.

Typically, the novel random copolymer described above have a weight-averaged molecular weight (Mw) in the range of about 3,000 to about 500,000 g/mol or in another embodiment of about 4,000 to about 200,000, or in another embodiment from about 5,000 to about 150,000. The polydispersity (PD) (Mw/Mn) may range from about 1.0 to about 8, or about 1.5 to about 4, or about 1.5 to about 3.0. Molecular weight, both Mw and Mn, can be determined by, for example, by gel permeation chromatography using a universal calibration method, calibrated to polystyrene standards.

The novel random copolymer described above containing repeat unit (1), (2) and (3) can be used in a composition containing a single random copolymer or as blends of random copolymers with differing molecular weight, differing concentrations of a repeat unit of structure (1) containing a benzocyclobutene pendant group, differing comonomer ratios, etc. The repeat unit of structure (1) containing the benzocyclobutene can also be employed with varying amounts of repeat units of structures (2) and (3) without while maintaining the neutrality of a film cast and crosslinked on a substrate. For example, as a non-limiting example, units derived from styrene and methyl methacrylate derived repeat units can be varied quite substantially while maintaining neutrality towards a block copolymer containing the corresponding repeat units in a large range of blending compositions. This allows one to optimize a neutral layer for instance by adjusting the composition of a binary blend containing two different neutral polymers containing different ratios of repeat units so as to maximize the effectiveness of a particular self-directed approach such a graphoepitaxy or chemoepitaxy in imparting pattern rectification and/or pattern multiplication for a given array of repeating features such as L/S or CH patterns. A single polymer may also be used in the novel composition. In one embodiment of the present invention the neutral layer composition comprises a blend of two or more different composition of the novel polymer. The composition may comprise a blend of two or more polymers of differing mole % concentration of the units of structure (1), (2) and (3). As an example, the composition comprises a first and second polymer of differing mole ratios of the monomeric units; a first polymer where the unit of structure (1) is from about 5 mole % to about 40 mole %, structure of unit (2) is from about 10 mole % to about 90 mole % and structure (3) is from about 10 mole % to about 90 mole %; a second polymer where the unit of structure (1) is from about 10 mole % to about 50 mole %, structure of unit (2) is from about 20 mole % to about 80 mole % and structure (3) is from about 20 mole % to about 80 mole %.

The novel random copolymer described above containing repeat unit (1) and (2) may be used in a composition containing a single random copolymer of this type or as blends of random copolymers with differing molecular weight, differing concentrations of a repeat unit (1) containing a benzocyclobutene pendant group, differing comonomer ratios, etc. The repeat unit (1) containing the benzocyclobutene can also be employed with varying amounts of other monomeric units, for example methylmethacrylate units can be varied quite substantially while maintaining pinning towards a block copolymer containing the corresponding repeat units in a large range of blending compositions. This allows one to optimize a neutral layer for instance by adjusting the composition of a binary blend containing two different pinning polymers containing different ratios of repeat units so as to maximize the effectiveness of a particular self-directed approach such a graphoepitaxy or chemoepitaxy in imparting pattern rectification and/or pattern multiplication for a given array of repeating features such as L/S or CH patterns. A single polymer may also be used in the novel composition. In one embodiment of the present invention the neutral layer composition comprises a blend of two or more different composition of the novel polymer. The composition may comprise a blend of two or more polymers of differing mole % concentration of the units of structure (1), and (2). As an example, the composition comprises a first and second polymer of differing mole ratios of the monomeric units; a first polymer where the unit of structure (1) is from about 10 mole % to about 90 mole %, and structure of unit (2) is from about 10 mole % to about 90 mole %; a second polymer where the unit of structure (1) is from about 15 mole % to about 80 mole %, structure of unit (2) is from about 15 mole % to about 85 mole %.

The novel random copolymer described above containing repeat unit (1) and (3) may be used in a composition containing a single random copolymer of this type or as blends of random copolymers with differing molecular weight, differing concentrations of a repeat unit (1) containing a benzocyclobutene pendant group, differing comonomer ratios, etc. The repeat unit (1) containing the benzocyclobutene can also be employed with varying amounts of other monomeric units, for example styrene units can be varied quite substantially while maintaining pinning towards as a non-limiting example a block copolymer of polystyrene and methylmethacrylate in a large range of blending compositions. This allows one to optimize a pinning layer for instance by adjusting the composition of a binary blend containing two different pinning polymers containing different ratios of repeat units so as to maximize the effectiveness of a particular self-directed approach such a graphoepitaxy or chemoepitaxy in imparting pattern rectification and/or pattern multiplication for a given array of repeating features such as US or CH patterns. A single polymer may also be used in the novel composition. In one embodiment of the present invention the crosslinked pinning layer is coated from a composition comprises a blend of two or more different novel polymers having at least one repeat unit of structure (1), which can be coated and subsequently crosslinked on a substrate or the surface and subsequently patterned. The pinning patterned areas are generated by patterning the coating with an overlying patterned resist using the resist as a template to selectively etch the areas not protected by overlying resist with either a wet or dry chemical etch process.

The composition may comprise a blend of 2 or more polymers of differing mole % concentration of the units of structure (1), and (3). As an example, the composition comprises a first and second polymer of differing mole ratios of the monomeric units; a first polymer where the unit of structure (1) is from about 5 mole % to about 80 mole %, and structure (3) is from about 20 mole % to about 95 mole %; a second polymer where the unit of structure (1) is from about 10 mole % to about 80 mole %, structure of unit 3 is from about 20 mole % to about 90 mole %.

The solid components of these novel neutral layer or pinning composition are mixed with a solvent or mixtures of solvents that dissolve the solid components. Suitable solvents may include, for example, a glycol ether derivative such as ethyl cellosolve, methyl cellosolve, propylene glycol monomethyl ether (PGME), diethylene glycol monomethyl ether, diethylene glycol monoethyl ether, dipropylene glycol dimethyl ether, propylene glycol n-propyl ether, or diethylene glycol dimethyl ether; a glycol ether ester derivative such as ethyl cellosolve acetate, methyl cellosolve acetate, or propylene glycol monomethyl ether acetate (PGMEA); carboxylates such as ethyl acetate, n-butyl acetate and amyl acetate; carboxylates of di-basic acids such as diethyloxylate and diethylmalonate; dicarboxylates of glycols such as ethylene glycol diacetate and propylene glycol diacetate; and hydroxy carboxylates such as methyl lactate, ethyl lactate (EL), ethyl glycolate, and ethyl-3-hydroxy propionate; a ketone ester such as methyl pyruvate or ethyl pyruvate; an alkoxycarboxylic acid ester such as methyl 3-methoxypropionate, ethyl 3-ethoxypropionate, ethyl 2-hydroxy-2-methyl propionate, or methylethoxypropionate; a ketone derivative such as methyl ethyl ketone, acetyl acetone, cyclopentanone, cyclohexanone or 2-heptanone; a ketone ether derivative such as diacetone alcohol methyl ether; a ketone alcohol derivative such as acetol or diacetone alcohol; a ketal or acetal like 1,3 dioxalane and diethoxypropane; lactones such as butyrolactone; an amide derivative such as dimethylacetamide or dimethylformamide, anisole, and mixtures thereof. Preferred solvents are propylene glycol monomethyl ether acetate (PGMEA), propylene glycol monomethyl ether (PGME), anisole, cyclohexanone and butyrolactone and mixtures therefore.

The novel composition have a wt % content of novel random copolymer or mixture of random copolymers comprised of repeat unit (1) which may range from 0.1 to 5 wt %, or about 0.2 to 2 wt % dissolved in a suitable solvent as described above.

The neutral layer or pinning composition may further comprise surfactants as additives.

The block copolymer for use in directed self-assembly in conjunction with the novel neutral layer composition can be any block copolymers which can form domains through self-assembly. The microdomains are formed by blocks of the same type which tend to self associate. Typically, block copolymer employed for this purpose are polymers in which the repeat units derived from monomers are arranged in blocks which are different compositionally, structurally or both and are capable of phase separating and forming domains. The blocks have differing properties which can be used to remove one block while keeping the other block intact on the surface, thus providing a pattern on the surface. Thus, the block may be selectively removed by plasma etching, solvent etching, developer etching using aqueous alkaline solution, etc. In block copolymers based on organic monomers, one block can be made from polyolefinic monomers including polydienes, polyethers including poly(alkylene oxides) such as poly(ethylene oxide), poly(propylene oxide), poly(butylene oxide) or mixtures thereof; and, the other block can be made from different monomers including poly((meth)acrylates), polystyrenes, polyesters, polyorganosiloxanes, polyorganogermanes, and or mixtures thereof. These blocks in a polymer chain can each comprise one or more repeat units derived from monomers. Depending on the type of pattern needed and methods used different types of block copolymers may be used. For instance, these may consist of diblock copolymers, triblock copolymers, terpolymers, or multiblock copolymers. The blocks of these block copolymers may themselves consist of homopolymers or copolymers. Block copolymers of different types may also be employed for self-assembly, such as dendritic block copolymers, hyperbranched block copolymers, graft block copolymers, organic diblock copolymers, organoic multi-block copolymers, linear block copolymers, star block copolymers amphiphilic inorganic block copolymers, amphiphilic organic block copolymers or a mixture consisting of at least block copolymers of different types.

The blocks of organic block copolymer may comprise repeat units derived from monomers such as C-2 to C-30 olefins, (meth)acrylate monomers derived from $C_{1-30}$ alcohols, inorganic-containing monomers including those based on Si, Ge, Ti, Fe, Al. Monomers based on C-2 to C-30 olefins can make up a block of high etch resistance alone or do so in combination with one other olefinic monomer. Specific example of olefinic monomers of this type are ethylene, propylene, 1-butene, 1,3-butadiene, isoprene, dihydropyran, norbornene, maleic anhydride, styrene, 4-hydroxy styrene, 4-acetoxy styrene, 4-methylstyrene, alpha-methylstyrene or mixtures thereof. Examples of highly etchable units can be derived from (meth)acrylate monomers such as (meth)acrylate, methyl (meth)acrylate, ethyl (meth)acrylate, n-propyl (meth)acrylate, isopropyl (meth)acrylate, n-butyl (meth)acrylate, isobutyl (meth)acrylate, n-pentyl (meth)acrylate, isopentyl (meth)acrylate, neopentyl (meth)acrylate, n-hexyl (meth)acrylate, cyclohexyl (meth)acrylate, isobornyl (meth) acrylate, hydroxyethyl (meth)acrylate or mixtures thereof.

Examples of a block copolymer containing high etch resistant block and a highly etchable block are block copolymer where one of the highly etch resistant block is comprised primarily of primarily of units derived from vinyl aryl monomers such as styrenic monomer, vinyl naphthalenic, vinyl anthracenic and the like, and the highly etchable block is derived from olefinic monomers containing oxygen derived such as the non-limiting examples of, acrylate acid, methacrylic acid, alkyl acrylates, alkyl methacrylates, fumaric acid, alkyl fumarates, itaconic acid, alkyl Itaconoates, vinyl alkyl ether, vinyl esters of alkylcarboxylic acid and other similar polar repeat units derived from olefins which contain oxygen. A more specific description of one of these types of block copolymer is a block copolymer comprised of a block of polar aliphatic repeat unit has the (meth)acrylate structure (2a) with a high etch rate and a block of aromatic styrenic repeat units of structure (3a) with low etch rate in a plasma comprising.

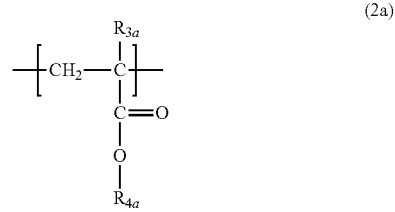

(2a)

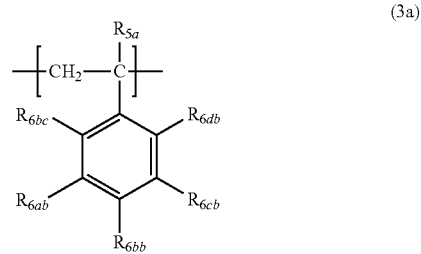

(3a)

where $R_{3a}$ are independently selected from hydrogen, a C-1 to C-4 fluoroalkyl or a C-1 to C-4 alkyl, $R_{4a}$ is selected a C-1 to C-20 alkyl, a halide, a C-1 to C-10 fluoroalkyl group, or a (trialkylsilyl)alkylene group, $R_5$ and $R_{5a}$ are independently selected from hydrogen, a C-1 to C-4 alkyl, or a C-1 to C-4 fluoroalkyl, $R_6$, $R_{6a}$, $R_{6b}$, $R_{6c}$, $R_{6d}$ $R_{6bc}$, $R_{6ab}$, $R_{6bb}$, $R_{6cb}$, and $R_{6db}$, are independently selected from the group consisting of hydrogen, a C-1 to C-20 alkyl, a C-1 to C-20 alkoxy, a C-1 to C-10 fluoroalkyl, a C-1 to C-10 fluoroalkoxy, a trialkylsilyl group, a (trialkylsilyl)alkylene group, and a (trialkylsilyl)alkyleneoxy group where; $R_{3a}$ is hydrogen, a C-1 to C-4 fluoroalkyl, a halide, or a C-1 to C-4 alkyl, $R_{4a}$ is a C-1 to C-20 alkyl, or a C-1 to C-10 fluoroalkyl group. In a more specific aspect of this embodiment the random copolymer is one in which $R_1$ is H or methyl, $R_2$ is H and G is a C-2 to C-5 alkylene moiety $R_2$ is H, and further where $R_5$ is hydrogen, $R_6$, $R_{6a}$, $R_{6b}$, $R_{6c}$ and $R_{6d}$ are independently hydrogen, a C-1 to C-4 alkyl, or a C-1 to C-4 alkoxy. In another more specific embodiment of this aspect, the block copolymer is one where $R_{3a}$ is hydrogen, or a C-1 to C-4 alkyl, and R4a is a C-1 to C-20 alkyl, or a C-1 to C-10 fluoroalkyl group and $R_{5a}$ hydrogen, $R_{6bc}$, $R_{6ab}$, $R_{6bb}$, $R_{6cb}$, and $R_{6db}$, are independently selected from the group consisting of hydrogen, a C-1 to C-20 alkyl, a C-1 to C-10 fluoroalkyl.

Specific non-limiting examples of other block copolymers that are useful for graphoepitaxy, chemoepitaxy or pinned chemoepitaxy as used for directed self-assembly on a patterned neutral layer, are poly(styrene-b-vinyl pyridine), poly (styrene-b-butadiene), poly(styrene-b-isoprene), poly(styrene-b-methyl methacrylate), poly(styrene-b-alkenyl aromatics), poly(isoprene-b-ethylene oxide), poly(styrene-b-(ethylene-propylene)), poly(ethylene oxide-b-caprolactone), poly(butadiene-b-ethylene oxide), poly(styrene-b-t-butyl (meth)acrylate), poly(methyl methacrylate-b-t-butyl methacrylate), poly(ethylene oxide-b-propylene oxide), poly(styrene-b-tetrahydrofuran), poly(styrene-b-isoprene-b-ethylene oxide), poly(styrene-b-dimethylsiloxane), poly(methyl methacrylate-b-dimethylsiloxane), or a combination comprising at least one of the above described block copolymers.

All these polymeric materials share in common the presence of at least one block which is rich in repeat units resistant to etching techniques typically employed in manufacturing IC devices and at least one block which etches rapidly under these same conditions. This allows for the directed self-assembled polymer to pattern transfer onto the substrate to affect either pattern rectification or pattern multiplication. Another Typically, the block copolymers employed for the directed self-assembly such as in graphoepitaxy, chemoepitaxy or pinned chemoepitaxy have a weight-averaged molecular weight ($M_w$) in the range of about 3,000 to about 500,000 g/mol and a number averaged molecular weight ($M_n$) of about 1,000 to about 60,000 and a polydispersity ($M_w/M_n$) of about 1.01 to about 6, or 1.01 to about 2 or 1.01 to about 1.5. Molecular weight, both $M_w$ and $M_n$, can be determined by, for example, gel permeation chromatography using a universal calibration method, calibrated to polystyrene standards. This ensures that the polymer blocks have enough mobility to undergo self-assembly when applied to a given surface either spontaneously, or by using a purely thermal treatment, or through a thermal process which is assisted by the absorption of solvent vapor into the polymer framework to increase flow of segments enabling self-assembly to occur.

Solvents suitable for dissolving block copolymers for forming a film can vary with the solubility requirements of the block copolymer. Examples of solvents for the block copolymer assembly include propylene glycol monomethyl ether acetate (PGMEA), ethoxyethyl propionate, anisole, ethyl lactate, 2-heptanone, cyclohexanone, amyl acetate, n-butyl acetate, n-amyl ketone (MAK), gamma-butyrolactone (GBL), toluene, and the like. In an embodiment, specifically useful casting solvents include propylene glycol monomethyl ether acetate (PGMEA), gamma-butyrolactone (GBL), or a combination of these solvents.

The block copolymer composition can comprise additional components and/or additives selected from the group consisting of: inorganic-containing polymers; additives including small molecules, inorganic-containing molecules, surfactants, photoacid generators, thermal acid generators, quenchers, hardeners, cross-linkers, chain extenders, and the like; and combinations comprising at least one of the foregoing, wherein one or more of the additional components and/or additives co-assemble with the block copolymer to form the block copolymer assembly.

The block copolymer composition is applied to a pattern of the novel neutral layer which has been defined on a surface by conventional lithography, where the neutral surface is a crosslinked coating formed from the novel composition. Upon application and solvent removal, the block copolymer then undergoes self-assembly directed by the specific pattern formed by conventional lithographic processing over the neutral layer through either actual topographical features or a patterned chemical difference of the substrate surface created by conventional lithographic process. Either pattern rectification maintaining the same resolution is achieved and/or pattern multiplication may also be achieved if multiple phase boundaries are formed between the features defined with conventional lithography, depending on the relative pitch of the pattern versus the microphase separation distance after standard IC processing to pattern transfer.

The application of the block copolymer by spinning techniques (including spin drying) can suffice to form the self-directed block copolymer assembly. Other methods of self-directed domain formation can occur during applying, baking, annealing, or during a combination of one or more of these operations. In this way, an oriented block copolymer assembly is prepared by the above method, having microphase-separated domains that comprise cylindrical microdomains oriented perpendicular to the neutral surface, or that comprise lamellar domains oriented perpendicular to the neutral surface. Generally, the microphase-separated domains are lamellar domains oriented perpendicular to the neutral surface, which provide parallel line/space patterns in the block copolymer assembly. The domains, so oriented, are desirably thermally stable under further processing conditions. Thus, after coating a layer of a block copolymer assembly including a useful diblock copolymer such as, for example, poly(styrene-b-methyl methacrylate), and optionally baking and/or annealing, the domains of the block copolymer will form on and remain perpendicular to the neutral surface, giving highly resistant and highly etchable regions on the surface of the substrate, which can be further pattern transferred in the substrate layers. The directed self-assembled block copolymer pattern is transferred into the underlying substrate using known techniques. In one example wet or plasma etching could be used with optional UV exposure. Wet etching could be with acetic acid. Standard plasma etch process, such as a plasma comprising oxygen may be used; additionally argon, carbon monoxide, carbon dioxide, $CF_4$, $CHF_3$, may be present in the plasma. FIGS. 1a-1c illustrate a process where the neutral layer is modified to define a patterned chemical affinity, FIG. 1a. The block copolymer is then coated over a chemically modified neutral layer and annealed to form domains perpendicular to the substrate surface, FIG. 1b. One of the domains is then removed to form a pattern on the surface of the substrate, FIG. 1c.

In the present invention the initial photoresist pattern used for forming the directed self-assembly pattern can be defined using either negative or positive photoresists, or either positive tone or negative tone development processes, and imageable using any conventional lithographic techniques, such as e-beam, ion beam, x-ray, EUV (13.5 nm), broadband, or UV (450 nm-10 nm) exposure, immersion lithography, etc. In one embodiment the present invention is particularly useful for 193 nm imagewise exposure using either dry lithography or immersion lithography. For 193 nm lithography a commercially available positive 193 nm photoresist can be employed such as the non-limiting example of AZ AX2110P (available from AZ Electronic Materials USA Corp, Somerville, N.J.), photoresist from Shin-Etsu Chemical Corp., JSR Micro from Japan Synthetic Rubber, and other photoresists available from FujiFilm, TOK, etc. These photoresists may be developed after exposure, and post exposure baked using an aqueous alkaline developer comprising tetramethylammonium hydroxide to give a positive tone pattern or developed using an organic solvent such as n-amyl ketone (MAK), n-butyl acetate, anisole, etc. to give a negative tone pattern. Alternatively, also for 193 nm exposure, commercially available negative tone photoresists may be employed. One particular feature of the present invention is that when the novel composition is used in the embodiment where it works as a neutral layer despite the high level of crosslinking of the neutral layer, unexpectedly neutrality of the neutral layer toward the block copolymer is maintained. The high level of crosslinking is required when processing steps occur, such as overcoating with photoresist, baking the photoresist, exposing the photoresist, developing the photoresist pattern with the developers employed as described above for each type of photoresist, stripping conditions, etc.; but the novel neutral film still retains neutrality thus allowing for proper orientation of the block copolymer domains between the topographical lithographic features. The neutrality is required to control the orientation of the block copolymer during the alignment process, such that the domains of the block copolymer will form on and remain perpendicular to the neutral surface, as shown in FIGS. 1a-1c. FIG. 1a-1c show how the block copolymer orients itself into domains perpendicular to the substrate and one of the domains is removes to give a pattern on the substrate.

The substrate over which the novel neutral layer or pinning layer composition of this invention are coated are any required by the device. In one example the substrate is a wafer coated with a layer of high carbon content organic layer with a coating of silicon or titanium containing ARC (high etch resistance to oxygen plasma) over it, which allows pattern transfer of the patterned block copolymer into these coatings. Suitable substrates include, without limitation, silicon, silicon substrate coated with a metal surface, copper coated silicon wafer, copper, aluminum, polymeric resins, silicon dioxide, metals, doped silicon dioxide, silicon nitride, silicon carbide, tantalum, polysilicon, ceramics, aluminum/copper mixtures, glass, coated glass; gallium arsenide and other such Group III/V compounds. These substrates may be coated with antireflective coating(s). The substrate may comprise any number of layers made from the materials described above.

For the present invention a variety of processes involving graphoepitaxy or (pinned) chemoepitaxy may be employed to achieve a directed self-assembly of the aforementioned block copolymer by using a crosslinked neutral layer derived from a novel composition of this invention containing structure (1) which is resistant to lithographic processes as described above, especially maintaining neutrality after crosslinking, to control the orientation of the block copolymers relative to the substrate; this directed self-assembly block copolymer coating is then used to form a high resolution pattern using plasma or wet etching to remove the highly etchable domains of the block copolymer. This pattern can then be further transferred into the substrate. In this manner, a variety of high resolution features may be pattern transferred into the substrate achieving either pattern rectification, pattern multiplication or both.

As an example, in graphoepitaxy applications, any structure such as a photoresist pattern, using any photoresist, is formed and imaged over the novel neutral layer coated on a substrate using standard lithographic techniques. Other neutral layers which are resistant to lithographic processes and maintain neutrality after crosslinking may be used. The pitch of topographical features imaged through standard lithography using a photoresist on top of a neutral layer is larger than the pitch of the block copolymer assembly. These topographical photoresist features are typically hardened by ultraviolet exposure, baking or a combination of both of these to avoid intermixing of the block copolymer with the photoresist. The hardening conditions are determined by the type of photoresist used. As an example hardening can be a bake for 2 minutes at 200° C. with or without a UV exposure. The block copolymer composition is used to form a coating and then treated to form self-directed domains as described previously. Consequently, the domains of the block copolymer assembly (either spontaneously, through solvent treatment or thermally by annealing) are forced by the constraints of the topographical pattern overlying the critical neutral layer to align in such a way to multiply the spatial frequency of the fine topographical photoresist pattern, that is domains of high etch rate and etch resistant regions are formed perpendicular to the substrate surface. This multiplication of special frequency is the number of repeating sets of features along a given direction of the topographical pattern. Thus, the resulting pattern in the block copolymer assembly (the spatial frequency of the patterned block copolymer assembly) can be doubled, tripled, even quadrupled relative to the spatial frequency of the original fine topographical pattern. The segregation of the domains occurs such that a structure comprising repeating sets of domains is formed between the patterned photoresist topography with a spatial frequency for the domains (given by the number of repeating sets of domains in the given direction) of at least twice that of the spatial frequency for the topographical pattern.

In one embodiment, the present invention relates to a process for using a positive tone photoresist pattern for graphoepitaxy. In this embodiment, the novel composition is one where the novel random copolymer composition can act as a neutral layer which is resistant to lithographic processes and maintain neutrality after crosslinking, as described herein. The process comprises forming a neutral layer by coating the novel neutral layer composition on a substrate surface; baking the neutral layer to form a crosslinked and neutral layer; providing a coating of a positive acting photoresist layer over the neutral layer; forming a positive pattern in the photoresist; optionally, hardening the positive photoresist pattern by hard baking, UV exposure or a combination of the two; applying a block copolymer comprising an etch resistant block and an etch labile block over the residual positive photoresist pattern and annealing the film stack until directed self-assembly governed by the residual photoresist feature and neutral layer occurs, such that the domains form perpendicular to the substrate surface; and, etching the block copolymer so that the etch labile blocks are removed producing a line multiplication of the original residual pattern. The neutral layer is such that no damage occurs to the neutral layer during lithographic processing, as described previously.

In another embodiment, the present invention relates to a process for using a negative tone photoresist pattern for use in graphoepitaxy. The novel compositions of this invention as described herein as acting as a neutral layer, may be used because they are resistant to lithographic processes and maintain neutrality after. The process comprises forming a neutral layer by coating the novel neutral layer composition on a substrate; baking the neutral layer to form a crosslinked and neutral layer; providing a coating of a negative acting photoresist layer over the neutral layer; forming a negative tone pattern in the photoresist; optionally, hardening the photoresist pattern by hardbaking, UV exposure or a combination of the two; applying a block copolymer comprising an etch resistant block and an etch labile block to the substrate containing the pattern and annealing the film stack until directed self-assembly governed by the residual photoresist feature and the neutral layer occurs, such that the domains form perpendicular to the substrate surface; and, etching the block copolymer so that the etch labile block are removed producing a line multiplication of the original residual pattern. The neutral layer is such that no damage occurs to the neutral layer during lithographic processing, as described previously.

In chemoepitaxy, a pinning layer provides a pinning surface feature in the novel neutral layer which has a particular chemical affinity towards a block of the block copolymer, and it is this affinity and the presence of the neutral layer which orients the alignment of the block copolymer. The novel compositions of this invention as described herein as acting as a neutral layer may be used as such in a chemoepitaxy because after crosslinking they are resistant to lithographic processes and maintain neutrality or alternatively may be a commercially available neutral layer. The pinning feature may be a patterned photoresist feature on the surface of the novel neutral layer or a patterned opening in the novel neutral layer or a patterned neutral layer whose surface has been suitably treated to provide a patterned pinning surface. Alternatively, this pinning features in a chemoepitaxy process may arise from patterning a crosslinked layer of the novel compositions comprising at least one random copolymer having at least one repeat unit of structure (1), which was coated and subsequently crosslinked on a substrate or the surface and subsequently patterned. The pinning patterned areas may be generated by patterning the coating with an overlying patterned resist using the resist as a template to selectively etch the areas not protected by overlying resist with either a wet or dry chemical etch process.

Alternatively, the pinning feature with the chemical difference can be created by any method, such as lithographic imaging of the photoresist and/or etching of the neutral layer to expose a patterned surface with a chemical difference, or any other combination of lithographic techniques. The pinning feature may also be created by chemical treatment of the patterned surface of the neutral layer, without removing the neutral layer. Typically, a stack is formed on the substrate comprising a neutral layer coated over a substrate, over which is coated a photoresist layer.

In one embodiment of a negative tone (where the unexposed region is removed to form a pattern) line multiplication chemoepitaxy, a coating of the novel compositions of this invention as described herein as acting as a neutral layer are coated on a substrate, such as on an antireflective substrate or any other type of substrate; the neutral layer is heated to form a crosslinked neutral layer; a coating of a photoresist layer is formed over the crosslinked neutral layer; and, the photoresist is imaged to form a pattern with an open or developed trench in the unexposed regions over the neutral layer and substrate stack. Typically a negative tone is obtained by using a negative photoresist which opens the unexposed regions or a positive photoresist which after forming a latent image in the photoresist uses an organic solvent to remove the unexposed regions, thus forming a trench with a narrow opening. A neutral layer which is resistant to lithographic processes and maintain neutrality after crosslinking may be used. Once the pattern is formed over the neutral layer, the trench is treated to have a chemical affinity. The chemical affinity can be achieved by any technique such as by removing the neutral layer, by wet etching or a plasma etch, or can be treated to form a surface with a particular chemical affinity to one of the blocks of the block copolymer. Typically an oxygen containing plasma is used to etch the neutral layer, thus forming a patterned neutral layer over the substrate. The photoresist is then removed. The photoresist may be removed with a wet stripper, such as an organic solvent stripper used for that particular photoresist or by an aqueous alkaline developer. The openings in the neutral layer have a chemical affinity to only one of the blocks in the block copolymer. As an example if the substrate surface is a silicon antireflective coating or an oxide, it will have an affinity towards the acrylate block and not to the styrene block of the block copolymer, thus forming a patterned pinning surface. One particular feature of the present invention is that despite the high level of crosslinking of the neutral layer, unexpectedly, neutrality of the neutral layer is maintained. The high level of crosslinking is required when overcoating with photoresist or developing the photoresist pattern with the developers employed, or stripping the photoresist, as described above for each type of photoresist; thus allowing for proper orientation of the block copolymer domains between the pinning areas created by the above described process. The block copolymer composition is then applied over the patterned neutral layer to form a layer and treated (such as heating to anneal) to form a self-aligned block copolymer with domains of an etch resistant block and an etch labile block perpendicular to the substrate containing the pattern of neutral layer and removed or treated neutral layer; and, further etching the block copolymer so that the etch labile blocks are removed producing a line multiplication of the original lithographic pattern. Removal of one of the blocks may be by plasma or wet etching. Consequently, the resulting pattern in the block copolymer assembly (i.e., the spatial frequency of the patterned block copolymer assembly) can be doubled, tripled, even quadrupled relative to the spatial frequency of the original fine chemical pattern. The domains, so oriented in this manner, should be thermally stable under the processing conditions. For instance when a layer of a block copolymer assembly including a useful diblock copolymer such as, for example, poly(styrene-b-methylmethacrylate), is coated on a chemically patterned neutral layer, the methyl methacrylate block segments will preferentially interact with the areas of the neutral layer which have been etched or treated; this creates pinning sites which constrain the domains of the block copolymer between the pinning sites, and the novel neutral layer forces the block segments of the block copolymer to remain perpendicular to the neutral surface and are constrained by the chemical pattern in the neutral layer. The domains form by lateral segregation of the blocks on the neutral layer between the constraining chemical patterns in the neutral layer. The segregation of the domains occurs such that a structure comprising repeating sets of domains is formed over the chemically patterned neutral layer with a spatial frequency for the domains (given by the number of repeating sets of domains in the given direction) of at least twice that of the spatial frequency for the original chemical pattern in the neutral layer. Finally, as before the directed self-assembled block copolymer pattern in transferred into the underlying substrate using standard plasma or wet etch processes.

In one embodiment of a positive tone line multiplication chemoepitaxy, a conventional positive photoresist may be used to create chemical pinning. This is accomplished by coating a positive photoresist as described previously on a crosslinked coating of novel compositions of this invention as described herein as acting as a neutral layer and imaging the photoresist such that the image is overexposed, thus reducing the dimensions of the photoresist pattern to create very shallow residual photoresist features, such as residual lines on which the block polymer may be applied. This very shallow feature has very little topography, about the order of 10 nm to 100 nm width and 5 nm to 30 nm height. These residual features act as a pinning area over the neutral layer when the block copolymer is applied to the surface of the neutral layer with these residual features remaining. As described above, the block copolymer form directed self-aligned domains using the residual features as pinning areas and neutral layer forces the alignment to give domains perpendicular to the substrate. Finally, as before the directed self-assembled block copolymer pattern in transferred into the underlying substrate using standard plasma or wet etch processes. In this approach, instead of a photo-resist the pinning pattern could be produced instead by a patterned crosslinked layer of a composition containing a repeat unit of structure (1) which is described herein as capable of forming a crosslinked pinning layer. The pattern in the crosslinked pinning layer would be produced by patterning with an overlying patterned resist and etching away the pinning areas not covered by the patterned resist with a wet or dry etching process.

In detail, FIGS. 2-4 describe novel processes that use the novel neutral underlayer to obtain high resolution features of the order of nanometers using directed self-assembly of block copolymers.

In the present processes, any type of substrate may be used. As an example, a substrate which has a coating of high carbon underlayer and a silicon antireflective coating may be used as a substrate. The high carbon underlayer can have a coating thickness of about 20 nm to about 2 microns. Over this is coated a silicon antireflective coating of about 10 nm to about 100 nm. The novel neutral layer composition is used to form a coating over the silicon antireflective coating. The neutral layer is coated and baked to form a crosslinked layer of thickness of about 3 nm to about 30 nm, or about 4 nm to about 20 nm, or about 5 nm to about 20 nm, or about 10 nm to about 20 nm. Over the crosslinked neutral layer is coated a photoresist which is formed and imaged using conventional techniques, such as spin coating, baking, and forming an image. FIGS. 2a-2i illustrate a negative tone line multiplication process. FIG. 3a-3g illustrate a positive tone line multiplication process. FIG. 4a-4d illustrate process for contact hole multiplication.

FIG. 2a-FIG. 2i illustrate a novel process for forming line multiplication using a negative tone process. A multilayer stack is formed on a substrate in FIG. 2a, where the stack comprises a substrate comprising a high carbon underlayer and a silicon antireflective coating layer, the novel crosslinked neutral layer and a photoresist layer. Any substrate may be used. Any neutral layer which is resistant to lithographic processes and maintains neutrality after crosslinking may be used such as the novel compositions of this invention as described herein as acting as a neutral layer. The photoresist may be any that is available such as 193 nm photoresist, immersion 193 nm photoresist, e beam photoresist, EUV photoresist, 248 nm photoresist, broadband, 365 nm, 436 nm, etc. The photoresist layer is imaged to form a pattern using conventional techniques. A negative tone photoresist may be used or a positive tone photoresist that uses an organic solvent to develop away the unexposed regions to form very narrow trenches may be used, as shown in FIG. 2b. The novel underlayer is treated to form a pinning surface with a specific chemical affinity to one of the blocks of the block copolymer, using techniques such as plasma etching to remove the layer, plasma etching to modify the surface of the layer, or chemically treating the layer by further deposition of a material or any other pinning methods. A plasma comprising oxygen may be used to remove the neutral layer, as shown in FIG. 2c. The photoresist is then stripped away using solvent stripper or plasma etching, as shown in FIG. 2d. Solvents such as any organic solvents known for removing photoresists may be used, such as PGMEA, PGME, ethyl lactate, etc. The photoresist may also be removed by developing the photoresist pattern in aqueous alkaline developer as commonly used in removing exposed photoresists. The crosslinked coating of the novel compositions of this invention as described herein as acting as a neutral layer may still maintains its neutrality after the photoresist process steps. Over the patterned neutral layer, FIG. 2e, the composition comprising the block copolymer is coated and treated (such as annealing) to form a self-directed alignment pattern of alternating segments of the block copolymer. A layer which is neutral is required to cause the alignment of the block copolymer to give regions of high etch resistance and regions of low etch resistance, such that pattern multiplication can be achieved, as shown in FIG. 1e; if the neutral layer was not sufficiently neutral then an undesirable orientation parallel to the surface would be achieved. A subsequent etch then removes the highly etchable blocks of the block copolymer, leaving a patterned surface with very high resolution, as shown in FIG. 2f. Typical etch to remove one of the blocks would be a wet or plasma etch as described previously. The pattern may then be transferred in the lower stack layers by plasma etching, as shown in FIG. 2g-2i, using etchants for the antireflective coating stack. Typical etch would be a plasma etch dependent on the substrate.

Figure 3A:
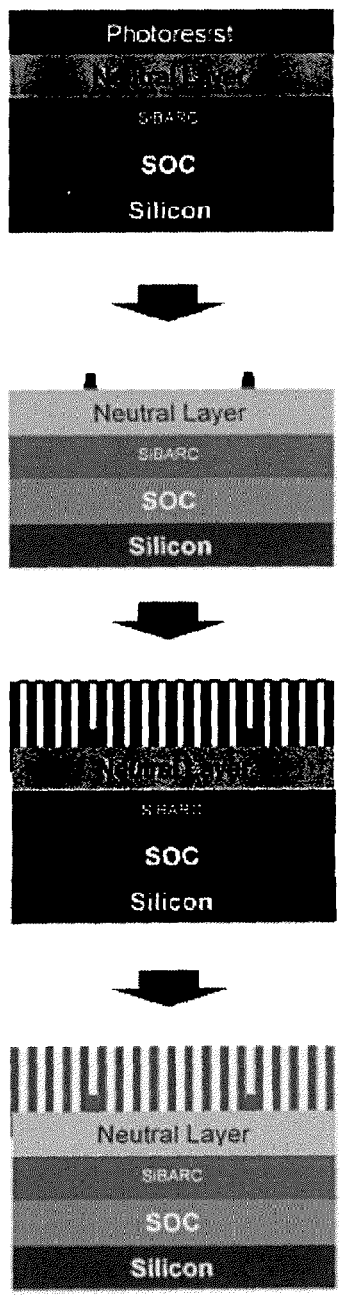
Figure 3B:
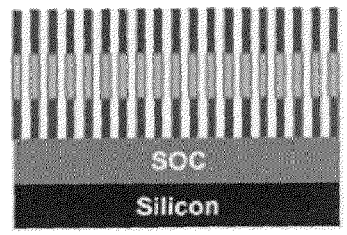
Figure 3C:
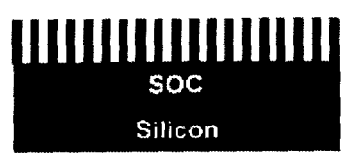
Figure 3D:

FIGS. 3a to 3g illustrates a process employing the embodiment of this invention which acts as neutral layer for forming line multiplication using a positive tone process. A multilayer stack is formed on a substrate the novel neutral layer and a photoresist layer in FIG. 3a, where the substrate comprises a high carbon underlayer and a silicon antireflective coating layer. The photoresist may any that are available such as 193 nm photoresist, immersion 193 nm photoresist, e beam photoresist, EUV photoresist, 248 nm photoresist, etc. The photoresist layer is imaged to form a pattern using conventional techniques. A positive tone photoresist is used to form fine photoresist lines, as shown in FIG. 3b. In some cases the photoresist is overexposed, that is given a high energy dose, to form very fine pattern. The very fine photoresist pattern over a coating of the novel neutral compositions described herein is used to form a self-aligned pattern using the block copolymer. The composition comprising the block copolymer is coated and treated (such as annealing) to form a self-directed alignment pattern of alternating segments of the block copolymer. A layer which is neutral is required to cause the alignment of the block copolymer to give regions of high etch resistance and regions of low etch resistance, such that pattern multiplication can be achieved, as shown in FIG. 3c; if the neutral layer was not sufficiently neutral then an undesirable orientation perpendicular to one shown would be achieved. A subsequent etch then removes the highly etchable blocks of the block copolymer, leaving a patterned surface with very high resolution, as shown in FIG. 3d. Typical etch would be a wet or plasma etch as described previously. The pattern may then be transferred in the lower stack layers by plasma etching, as shown in FIG. 3e-g. Typical etch would be plasma etch dependent on the substrate.

Figures 4A, 4B, 4C, 4D:
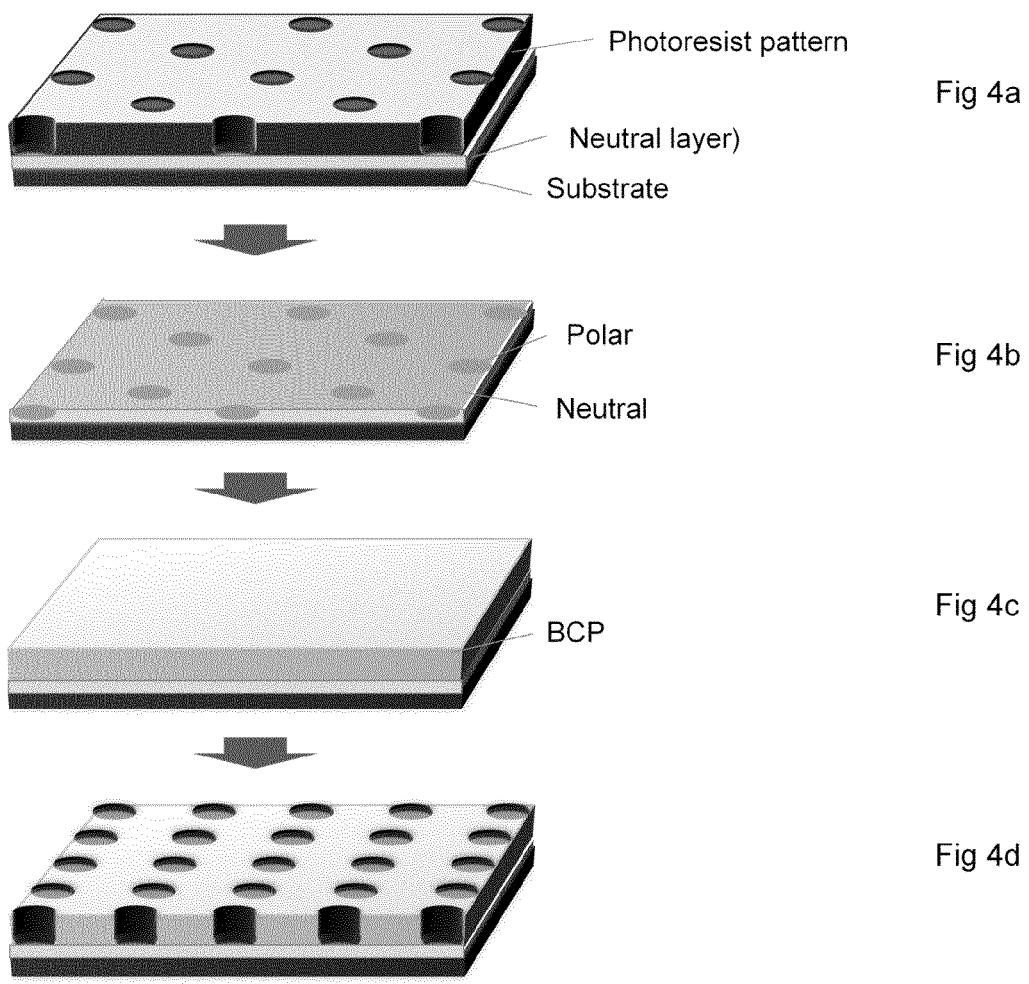
FIG. 4a-4d show a contact hole process.

FIG. 4a-4d illustrates a novel process for forming contact hole multiplication using a chemoepitaxy process employing the embodiment of this invention where novel composition acts as a neutral layer. A multilayer stack is formed on a substrate, where the stack comprises a substrate (such as a silicon antireflective coating layer, a titanium antireflective coating, silicon oxide, etc,), the novel neutral layer and a photoresist layer. The photoresist may be any that are available such as 193 nm photoresist, immersion 193 nm photoresist, e beam photoresist, EUV photoresist, 248 nm photoresist, etc. The photoresist layer is imaged to form a pattern using conventional techniques, FIG. 4a. The novel underlayer is treated to form a pinning surface using techniques such as plasma etching to remove the layer, plasma etching to modify the surface of the layer, or chemically treating the layer by further deposition of a material or any other pinning methods such as the application of a one of the novel composition described herein as acting as a pinning layer. A plasma comprising oxygen may be used to remove the neutral layer, as shown in FIG. 4b. The photoresist is then stripped away using solvent stripper or plasma etching. Solvents such as any organic solvents known for removing photoresists may be used, such as PGMEA, PGME, ethyl lactate, etc. may be used. The photoresist may also be used by developing the pattern in aqueous alkaline developer used in removing exposed photoresists. The neutral layer on the substrate still maintains its neutrality after the photoresist processing steps. Over the patterned neutral layer, FIG. 4c, the composition comprising the block copolymer is coated and treated (such as annealing) to form a self-directed alignment contact hole pattern of alternating segments of the block copolymer. A layer which remains neutral is required to cause the desired orientation of the block copolymer to give regions of high etch resistance and regions of low etch resistance, such that pattern multiplication can be achieved; if the neutral layer was not sufficiently neutral then an undesirable orientation perpendicular to one shown would be achieved. A subsequent etch then removes the highly etchable blocks of the block copolymer, leaving a patterned surface with very high resolution, as shown in FIG. 4d. Typical etch would be a wet or plasma etch as described previously. The pattern may then be transferred in the lower stack layers by plasma etching. Typical etch would be plasma etch dependent on the substrate. This process can be used for both pattern rectification and pattern pitch frequency multiplication.

The novel neutral layer or pinning composition are coated on a substrate and heated once to remove the solvent (optionally) and heated a second time to crosslink the film. Typical film thickness range from about 3 nm to about 50 nm after heating, or about 3 nm to about 30 nm, or about 4 nm to about 20 nm, or about 5 nm to about 20 nm, or about 10 nm to about 20 nm. To remove solvent on the substrate, the film can be heated at temperatures ranging from about 80° C.-220° C., 150° C.-180° C., or from about 160° C.-175° C., or about 165° C.-170° C.

Generally, the optional heating time to remove solvent from a film cast on a substrate is 1-10 minutes, or in another embodiment 2-5 minutes.

After the optional solvent removal bake is complete, or in a first bake if the solvent removal bake is not needed, a crosslinking bake is done at between about 180° C. to about 350° C., or in another embodiment between about 220° C. to about 350° C., or in another embodiment between about 220° C. to about 300° C., or in another embodiment between about 250° C. to about 280° C. or in another embodiment about 250° C. to about 350° C. The heating time to crosslink the polymer film is 1-10 minutes, or in another embodiment 2-5 minutes Once the cross-linked film has been formed the coating may be used for further processing to finally form a pattern using any self-directed assembly techniques. Examples of such techniques are graphoepitaxy, standard chemoepitaxy, chemoepitaxy with pinning, etc. The cross-linked neutral layers formed by the novel neutral layer composition remain neutral despite any damage that might occur during the lithographic processes where the crosslinked neutral layer is used, such as dissolution from organic solvents (such as solvents used to form coatings above the neutral layer, solvent developers, etc), dissolution in aqueous alkaline developers, damage from processes used to image the photoresist coated over the neutral layer (such as e-beam, euv, deep uv, etc), or dissolution in photoresist strippers. The crosslinked layers are not soluble in solvents such as those that are used to coat the photoresist, such as PGMEA, PGME, EL, etc.

In another aspect of this invention, the solvent removal bake and the crosslinking bake may be combined into one baking done at about 180° C. to about 350° C. or in another embodiment from about 250° C. to about 280° C., or from about 200° C. to about 300° C. or from about 200° C. to about 350° C., or from about 220° C. to about 300° C. or from about 220° C. to about 350° C., or from about 250° C. to about 350° C. The heating time to crosslink the polymer film is 1-10 minutes, or in another embodiment 2-5 minutes Once the cross-linked film has been formed the coating may be used for further processing to finally form a pattern using any self-directed assembly techniques. Examples of such techniques are graphoepitaxy, standard chemoepitaxy, chemoepitaxy with pinning, etc. The crosslinked neutral layers formed by the novel neutral layer composition remain neutral despite any damage that might occur during the lithographic processes where the crosslinked neutral layer is used, such as dissolution from organic solvents (such as solvents used to form coatings above the neutral layer, solvent developers, etc), dissolution in aqueous alkaline developers, damage from processes used to image the photoresist coated over the neutral layer (such as e-beam, euv, deep uv, etc), or dissolution in photoresist strippers. The crosslinked layers are not soluble in solvents such as those that are used to coat the photoresist, such as PGMEA, PGME, EL, etc.

In one aspect of this invention the novel composition comprised of a random copolymer comprised of a repeat unit (1) is employed in a process for forming a cross-linked layer on a substrate which is comprised of steps a) to c).
  a) coating of the composition comprised of a random copolymer comprised of a repeat unit (1) on a substrate form a layer;
  b) optionally heating the layer at a temperature between about 80° C. and about 180° C. to remove solvent;
  c) heating the layer at a temperature between about 220° C. and about 350° C. to form a cross-linked neutral layer;

In another aspect of this invention the novel composition comprised of a random copolymer comprised of a repeat unit (1) in any of the novel compositions described above it is employed in a process for forming a self-assembly block copolymer comprised of steps a) to e)
  a) coating the composition of comprised of a random copolymer comprised of a repeat unit (1) on a substrate to form a layer;
  b) optionally heating the layer at a temperature between about 80° C. and about 180° C. to remove solvent;
  c) heating the layer at a temperature between about 220° C. and about 350° C. to form a cross-linked neutral layer;
  d) applying a block copolymer layer over the cross-linked neutral layer
  e) annealing the block copolymer layer.

In another aspect of this invention the novel composition comprised of a random copolymer comprised of a repeat unit (1) which are described above as acting a neutral layer are employed in a forming an image using a graphoepitaxy process comprised of step a) to g):
  a) coating the novel composition comprised of a random copolymer comprised of a repeat unit (1) which are described above as acting a neutral layer on a substrate to form a layer;
  b) optionally heating the layer at a temperature between about 80° C. and about 180° C. to remove solvent;

c) heating the layer at a temperature between about 220° C. and about 350° C. to form a crosslinked neutral layer;
d) providing a coating of a photoresist layer over the crosslinked neutral layer;
e) forming a pattern in the photoresist;
f) applying a block copolymer comprising an etch resistant block and highly etchable block over the photoresist pattern and annealing until directed self-assembly occurs; and,
g) etching the block copolymer, thereby removing the highly etchable block of the copolymer and forming a pattern.

In another aspect of this invention the novel composition comprised of a random copolymer comprised of a repeat unit (1) which are described above as acting a neutral or pinning layers are employed in a process of forming an image comprised of step a) to i):

a) forming a coating of a crosslinked neutral layer, this layer may be brush neutral layer or a novel neutral layer formed by coating the novel composition of this comprised of a random copolymer comprised of a repeat unit (1) which are described above as acting a neutral layer on a substrate to form a layer and then optionally baking between about 80° C. and about 180° C. to remove solvent; followed by a non-optional crosslinking cure between about 200° C. and about 350° C. to form a crosslinked the crosslinked neutral layer.
b) providing a coating of a negative tune photoresist layer over the crosslinked neutral layer;
c) forming a pattern in the photoresist;
d) coating the novel composition comprised of a random copolymer comprised of a repeat unit (1) which are described above as acting as a pinning layer when crosslinked, to form a layer of thickness just thick enough to fill any voids in the patterned photoresist layer;
e) optionally heating the layer filling the voids at a temperature between about 80° C. and about 180° C. to remove solvent;
f) heating the layer filling the voids at a temperature between about 200° C. and about 350° C. to form a crosslinked pinning layer in the filled voids;
g) remove the photoresist;
h) applying a layer of a block copolymer comprising an etch resistant block and highly etchable block and annealing until directed self-assembly occurs;
i) etching the block copolymer, thereby removing the highly etchable block of the copolymer and forming a pattern.

In step of a) of this aspect of the invention the brush neutral layer applied to the substrate may be a brush neutral layer that can selectively graft to this substrate. Non-limiting examples of brush neutral layer that can selectively graft are described in U.S. Pat. No. 8,835,581 B2 which is incorporated by reference into this application.

In another aspect of this invention the novel composition comprised of a random copolymer comprised of a repeat unit (1) which are described above as acting a neutral layer in forming an image using a chemoepitaxy process comprising:

a) coating the composition of a novel composition comprised of a random copolymer comprised of a repeat unit (1) which are described above as acting a neutral layer on a substrate to form a layer;
b) optionally heating the layer at a temperature between about 80° C. to about 180° C. to remove solvent;
c) heating the layer at a temperature between about 220° C. to about 350° C. to form a crosslinked neutral layer;
d) providing a coating of a photoresist layer over the crosslinked neutral layer;
e) forming a pattern in the photoresist layer to remove the unexposed photoresist, thereby forming an uncovered crosslinked neutral layer region
f) treating the uncovered crosslinked neutral layer,
g) removing the photoresist,
h) applying a block copolymer comprising an etch resistant block and highly etchable block over the neutral layer and annealing until directed self-assembly occurs; and,
i) etching the block copolymer, thereby removing the highly etchable block of the copolymer and forming a pattern.

In another aspect of this invention the novel composition comprised of a random copolymer comprised of a repeat unit (1) which are described above as acting a pinning layer in forming an image using a chemoepitaxy process comprising:

a) coating of the novel composition comprised of a random copolymer comprised of a repeat unit (1) which are described above as acting a pinning layer on a substrate to form a layer;
b) optionally heating the layer at a temperature between about 80° C. and about 180° C. to remove solvent;
c) heating the layer at a temperature between about 220° C. and about 350° C. to form a cross-linked pinning layer;
d) providing a coating of a photoresist layer over the crosslinked pinning layer;
e) forming a pattern in the photoresist layer;
f) etching, to remove pinning later in the area without photoresist;
g) remove the photoresist;
h) forming a brush neutral layer at the area of non-pinning layer;
i) applying a block copolymer comprising an etch resistant block and highly etchable block over the neutral layer and annealing until directed self-assembly occurs; and,
g) etching the block copolymer, thereby removing the highly etchable block of the copolymer and forming a pattern.

In step of h) of this aspect of the invention the brush neutral layer applied to area not containing the pinning layer may be a brush neutral layer that can selectively graft to this area. Non-limiting examples of brush neutral layer that can selectively graft are described in U.S. Pat. No. 8,835,581 B2 which is incorporated by reference into this application.

In the above described graphoepitaxy and chemoepitaxy processes the photoresist pattern is formed by imaging lithography selected from a group consisting of e-beam, broadband, 193 nm immersion lithography, 13.5 nm, 193 nm, 248 nm, 365 nm and 436 nm. The photoresist may be a positive or negative photoresist.

The above processes describe novel processes that can be practiced. The process can use the novel neutral layer or novel pinning composition of the present invention.

Another aspect of this invention are the novel directing layers themselves formed by the above described compositions as follows:

In one embodiment a pinning directing layer for polar aliphatic polymer block domains of a block copolymer overlying the directing layer is formed by coating a composition of comprised of a polymer comprised of unit (1) on a substrate and crosslinking it, where this pinning layer has a total mole % of unit (1) and other (meth)acrylate derived repeat units equal or greater than about 60 mole % and further where the mole % composition of all repeat units does not exceed 100 mole %.

In another embodiment of a directing layer, a pinning layer for polar aliphatic polymer block domains of a block copolymer overlying the directing layer is formed by coating a composition comprised of a polymer comprised of unit (1) and unit (2) on a substrate and crosslinking it, where this pinning layer has a total mole % of unit (1) and unit (2) equal or greater than about 60 mole % and further where the mole % composition of all repeat units does not exceed 100 mole %.

In another embodiment of a directing layer, a pinning layer, for aromatic polymer block domains of a block copolymer overlying the directing layer is formed by coating a composition comprised of a polymer is comprised of unit (1), and unit (3), on a substrate and crosslinking it, where this pinning layer has a total mole % of unit (3) equal or greater than about 60 mole % and further where the mole % composition of all repeat units does not exceed 100 mole %.

In yet another embodiment of a directing layer, a neutral layer, for a block copolymer comprised of aromatic polymer block domains and polar aliphatic block domains overlying the directing layer, is formed by coating a composition comprised of a polymer comprised of repeat units (1), (2) and (3) where the total mole % of unit (1) and unit (2) ranges from about 45 mole % and about 55 mole % and where unit (3) ranges from about 45 mole % to about 55 mole %, and further where the total mole % composition of all repeat units does not exceed 100 mole %.

In yet another embodiment of this aspect of the invention a novel directing layer may be formed by coating any of the novel compositions described above containing at least one random copolymer having at least one repeat unit of structure (1) and crosslinking this layer to form a crosslinked directing layer.

In one aspect of this invention the crosslinked directing layer has a composition such that this directing layer will act as a pinning layer for one of the polymer block domains of a film overcoating this directing layer where the block copolymer is comprised block of polar aliphatic monomeric repeat units with a high etch rate and a block of monomeric aromatic units with low etch rate in a plasma comprising oxygen.

In general, a composition of the random polymer containing at least one repeat unit of structure (1) will act as pinning layer towards polar aliphatic block copolymer domains if the total amount of meth(acrylate) repeat units (1) and (2) is equal or greater to about 60 mole %, conversely, if this polymer contains an amount of about equal or greater than 60 mole % of it will act as a pinning layer for aromatic block copolymer domains, and if the total amount of meth(acrylate) repeat units (1) and (2) is about equal to the amount of the styrenic liked repeat unit (3) (i.e. about 45 to about 55 mole %) the crosslinked layer of polymer coated on a substrate will act as neutral layer towards the overlying block copolymer.

In another embodiment the novel crosslinked random polymer having at least one repeat unit of structure (1) is comprised of a block of styrenic like repeat units of structure (2a) with a high etch rate and a block of styrenic repeat units of structure (3a) with low etch rate in a plasma comprising oxygen; the detailed structures of possible block copolymers of this type are described in detail above. Similarly, the detailed structure of the random polymer containing at least one repeat unit of structure (1) leading crosslinked directing layer which are either pinning or neutral directing layer are described in detail above.

In summary, as per this descriptions:

Generally, compositions of the novel random copolymer containing at least one repeat unit of structure (1), which contain a total amount (meth)acrylate like repeat units such as repeat unit (1) or repeat unit (2) greater or equal to about 60 mole % will tend to act, when coated on a substrate and crosslinked, as pinning layer towards block copolymer domains derived from (meth)acrylate like repeat units (2a). In such compositions of the novel random copolymer containing at least one repeat unit of structure (1), the amount of repeat unit (2) may be 0 mole % and the total molar composition of such does not exceed 100 mole %.

Conversely, compositions of the novel random copolymer containing at least one repeat unit of structure (1), which contain a total amount (meth)acrylate like repeat units such as repeat unit (1) or repeat unit (2) less than about 60 mole %, and an amount of the styrenic like repeat unit of structure (3) equal or greater than about 60 mole % will tend to act, when coated on a substrate and crosslinked, as pinning layer towards block copolymer domains derived from styrenic like repeat units (3a). In such compositions of the novel random copolymer containing at least one repeat unit of structure (1) the amount of repeat unit (2) may be 0 mole % and the total molar composition of the copolymer does not exceed 100 mole %.

Finally, compositions of the novel random copolymer containing at least one repeat unit of structure (1) which which contain a total amount (meth)acrylate like repeat units such as repeat unit (1) or repeat unit (2) about equal to the amount of styrenic like repeat unit of structure (3) will tend to act, when coated on a substrate and crosslinked, as neutral layers towards block copolymer domains of a block copolymer containing (meth)acrylate like repeat units (2a) and styrenic like repeat units (3a). In such composition of the novel random copolymer containing at least one repeat unit of structure (1) the amount of repeat unit (2) may be 0 mole % and the total molar composition of repeat units does not exceed 100 mole %.

In one embodiment of the above pinning and neutral direction layer the crosslinking of the coated layer of the novel random copolymer containing at least one repeat unit of structure (1) is achieved upon heating the coating layer at a temperature between about 220 and about 300° C. such that this directing layer is insoluble in both organic solvents and aqueous bases.

The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLES

The molecular weight of the polymers was measured with a Gel Permeation Chromatograph. Chemicals, unless otherwise indicated, were obtained from the Sigma-Aldrich Corporation (St. Louis, Mo.).

Synthesis Example 1: Preparation of 2-iodoethyl methacrylate 40 g of sodium iodide and 0.22 g of 4-methoxyphenol were dissolved in 280 g of dry acetone. To this was added slowly 30.7 g of 2-chloroethyl methacrylate. The reaction mixture was fluxed for 3 days under nitrogen. After the reaction mixture was cooled to room temperature, 0.22 g of sodium hydroxide dissolved in 10 g of methanol and 10 g of activated carbon were added and the mixture was stirred for 2 hrs and filtered. Acetone was removed at room temperature with a rotary evaporator. The liquid obtained was dissolved in chloroform and washed first with aqueous diluted sodium thiosulfate solution and then DI water. After drying with sodium sulfate, chloroform was removed at room temperature with a rotary evaporator to obtain 35 g of desired 2-iodoethyl methacrylate. Proton NMR confirmed the structure.

Synthesis Example 2: Preparation of Ammonium Salt of 4-carboxybenzocyclobutene 7.6 gram of 4-carboxybenzocyclobutene was dissolved in 20 gram of THF in a 100 ml flask with a magnetic stir bar. To this was added 8.5 gram of tetramethylammonium pentahydrate dissolved in 22 g of methanol. After stirring for 1 hr, 45 g of sodium sulfate and 10 g of activated carbon were added and the reaction mixture was stirred at room temperature overnight. The mixture was filtered and the filtrate was poured into diethyl ether under stirring to obtain a yellowish solid which was dried in a 50° C. vacuum oven overnight. The solid was tetramethylammonium salt of 4-carboxybenzocyclobutene.

Synthesis Example 3: Preparation of Benzocyclobutene Methacrylate Monomer 13.9 g of the ammonium salt made above was dissolved in 150 g of DMSO. To this was added 12 g of 2-iodoethyl methacrylate diluted in 13 g of DMSO. After the reaction mixture was stirred at room temperature for 1 day about 500 ml of diethyl ether was added. The solid was filtered. The filtrate was washed first with aqueous diluted sodium thiosulfate solution and then DI water. After drying with sodium sulfate, diethyl ether was removed at room temperature with a rotary evaporator to obtain 11 g of desired benzocyclobutene methacrylate. Proton NMR confirmed the structure.

Synthesis Example 4: Synthesis of Copolymer for Neutral Layer in DSA 3.02 g of benzocyclobutene methacrylate prepared above, 6.5 g of methyl methacrylate (MMA), 6 g of styrene and 0.113 g of 2,2'-azobis(2-methylpropionitrile) (AIBN) were dissolved in 25 g of tetrahydrofuran (THF) in a 250 ml flask equipped with a magnetic stir bar and cold water condenser. After nitrogen purge for 30 min the flask was put into a 60° C. oil bath. Polymerization was carried out at this temperature for 19 hr and the solution was allowed to cool to room temperature. The polymer solution was slowly poured into about 200 ml of methanol with stirring. The polymer precipitated was isolated by filtering. The polymer was purified by dissolving in 20 g of tetrahydrofuran (THF) and re-precipitating in 200 ml of methanol. The polymer was finally dried in a 50° C. vacuum oven until constant weight (7.8 g obtained). GPC showed a Mw of 46230 and a Mn of 216161 g/mol. benzocyclobutene methacrylate in the polymer was estimated by proton NMR to be 14 mol %.

Testing Example 1: Curing Test

Copolymer obtained in Synthesis Example 4 was dissolved in PGMEA to prepare a 0.8 wt % solution. The solution was filtered with a 0.2 μm PTFE microfilter. The solution was spin cast on 6 inch silicon wafer at a rpm of 1500 for 30 seconds and the wafer was baked at 250° C. in air for 2 min. Film thickness was measured to be 506.4 Å by NanoSpec. After the wafer was puddle-rinsed with PGMEA for 30 seconds and baked at 110° C./1 min, the film thickness was 506.6 Å. This test showed that the polymer fully crosslinked to withstand solvent attack.

Testing Example 2: Neutrality Test

The same polymer solution from Testing Example 1 was spin cast on 6 inch silicon wafer at an rpm of 1500 for 30 seconds and the wafer was baked at 250° C. in air for 2 min. A diblock copolymer solution of polystyrene-b-poly(methyl methacrylate) in PGMEA (Mn for PS: 22000 g/mol and Mn for PMMA: 22000 g/mol. PDI: 1.02) was spin cast over the above wafer at 1500 rpm for 30 seconds and the wafer annealed in air at 250° C. for 2 min. Defect-free finger print of diblock polymer was observed under NanoSEM, indicating the cured polymer film was neutral to this diblock polymer.

The invention claimed is:
1. A composition comprising at least one random copolymer having at least one repeat unit of structure (1),

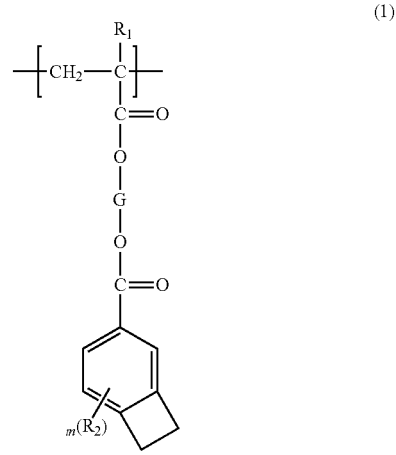

where (i) $R_1$ is selected from a group consisting of H, C-1 to C-4 alkyl, a C-1 to C-4 fluoroalkyl, and a halide; (ii) $R_2$ is selected from the group consisting of H, F, C-1 to C-8 alkyl and a C-1 to C-8 fluoroalkyl and where m ranges from 1 to 3; and (iii) G in structure (1) is a C-2 to C-10 alkylene moiety.

2. He composition of claim 1, wherein said composition is a composition, which
   (ia) forms a cross-linked layer on a coated substrate upon heating at a temperature between about 220° C. and about 300° C.;
   (iia) is insoluble in both organic solvents and aqueous bases; and affects self-assembly of the block domains of a block copolymer cast on top of said cross-linked layer and annealed.

3. The composition of claim 1, where said random copolymer further comprises at least one repeat units of structure (2) and at least one repeat unit of structure (3),

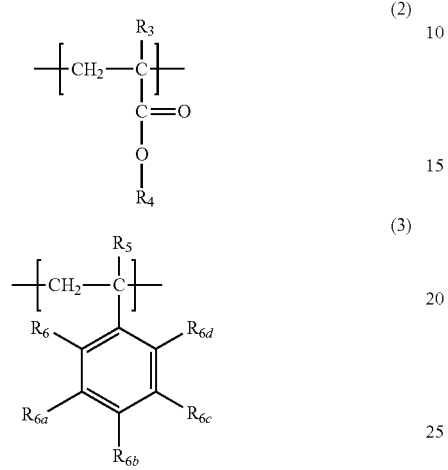

where $R_3$ is hydrogen, a C-1 to C-4 fluoroalkyl or a C-1 to C-4 alkyl, $R_4$ is a C-1 to C-20 alkyl, a halide, a C-1 to C-10 fluoroalkyl group, or a (trialkylsilyl)alkylene group, $R_5$ is hydrogen, a C-1 to C-4 alkyl, or a C-1 to C-4 fluoroalkyl, $R_6$, $R_{6a}$, $R_{6b}$, $R_{6c}$ and $R_{6d}$ are independently selected from the group consisting of hydrogen, a C-1 to C-20 alkyl, a C-1 to C-20 alkoxy, a C-1 to C-10 fluoroalkyl, a C-1 to C-10 fluoroalkoxy, a trialkylsilyl group, a (trialkylsilyl)alkylene group, and a (trialkylsilyl)alkyleneoxy group.

4. A process for forming an image on a substrate using graphoepitaxy comprised of step a) to f)
   a) coating the composition of claim 3 on a substrate to form a layer of said composition;
   b) heating the said layer of said composition at a temperature between about 220° C. and about 350° C. to form a cross-linked neutral layer;
   c) providing a coating of a photoresist layer over said cross-linked neutral layer;
   d) forming a photoresist pattern in said photoresist layer;
   e) applying a block copolymer comprising an etch resistant block and highly etchable block over said photoresist pattern and annealing until directed self-assembly of said block copolymer occurs forming a directed self-assembled layer of said block copolymer, with regions of this layer which are etch resistant and other regions which are highly etchable overlying the substrate; and,
   f) etching with a plasma said directed self-assembled layer of said block copolymer thereby removing said regions of said layer which are highly etchable overlying the substrate and forming an image in the substrate.

5. The process of claim 4 where between steps a) and b) the layer is heated at a temperature between about 80° C. and about 180° C. to remove solvent.

6. A process for forming an image by chemoepitaxy on a substrate comprising steps a) to i):
   a) coating the composition of claim 3, on a substrate to form a layer of said composition on said substrate;
   b) heating said layer of said composition at a temperature between about 220° C. and about 350° C. to form a cross-linked pinning layer on said substrate;
   c) providing a coating of a photoresist layer over said cross-linked pinning layer;
   d) forming a pattern photoresist layer thereby forming an uncovered cross-linked pinning layer region;
   e) etching, to remove said cross-linked pinning layer in said uncovered cross-linked pinning layer regions;
   f) removing said patterned photoresist layer, forming a substrate with an overlying patterned cross-linked pinning layer having areas which are covered and uncovered with cross-linked pinning layer;
   g) forming a brush neutral layer at the areas of said substrate having an overlying patterned cross-linked pinning layer only in said areas on the substrate which are uncovered by the pinning layer; forming a substrate with both pinning and neutral layer regions;
   h) applying a block copolymer layer comprising an etch resistant block and highly etchable block over said substrate with both pinning and neutral regions and annealing said block copolymer layer until directed self-assembly occurs forming a directed self-assembled layer of said block copolymer with regions which are etch resistant and other areas which are highly etchable; and,
   i) etching with a plasma said directed self-assembled layer of said block copolymer thereby removing said regions of said layer which are highly etchable overlying the substrate and forming in these regions an image in said substrate.

7. The process of claim 6 where between steps a) and b) the layer is heated at a temperature between about 80° C. and about 180° C. to remove solvent.

8. The composition of claim 1 where said random copolymer further comprises at least one repeat unit having structure (2),

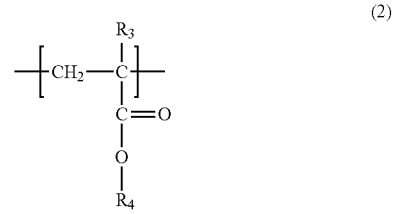

where $R_3$ is hydrogen, a C-1 to C-4 fluoroalkyl or a C-1 to C-4 alkyl, $R_4$ is a C-1 to C-20 alkyl, a halide, a C-1 to C-10 fluoroalkyl group, or a (trialkylsilyl)alkylene group.

9. A pinning directing layer for polar aliphatic polymer block domains of a block copolymer overlying the pinning directing layer formed by coating a composition of claim 4 on a substrate and crosslinking it, where this pinning directing layer has a total mole % of structure (1), and structure (2) equal or greater than about 60 mole %, and further where the total mole % composition of repeat units of structures (1) and (2) in the random copolymer does not exceed 100 mole %.

10. A process for forming an image on a substrate using graphoepitaxy comprised of step a) to h)
   a) forming a coating of a cross-linked neutral layer on a substrate;
   b) providing a coating of a negative tone photoresist layer over said cross-linked neutral layer;

c) forming a pattern in said negative photoresist layer forming a patterned photoresist layer which is comprised of voids in said negative photoresist layer corresponding to radiation unexposed regions of said negative photoresist film;

d) coating the composition of claim 8 on said patterned photoresist film to form a layer of said composition of a thickness which just fills the voids in said negative photoresist pattern;

e) heating said layer of said composition at a temperature between about 200° C. and about 350° C. to form a cross-linked pinning layer;

f) removing said negative photoresist pattern forming a patterned crosslinked pinning layer on said substrate;

g) applying a layer of a block copolymer over said pattered crosslinked layer wherein said block copolymer is one comprising an etch resistant block and highly etchable block and annealing until directed self-assembly of said layer of a block copolymer occurs forming a directed self-assembled layer of said block copolymer, with regions of this layer which are etch resistant and other regions which are highly etchable overlying the substrate;

h) etching with a plasma said directed self-assembled layer of said block copolymer thereby removing said regions of said layer which are highly etchable overlying the substrate and forming an image in said substrate.

11. The process of claim 10 where between steps d) and e) the layer is heated at a temperature between about 80° C. to about 180° C. to remove solvent.

12. A process for forming an image by chemoepitaxy on a substrate comprising steps a) to i):

a) coating the composition of claim 8 on a substrate to form a layer of said composition on said substrate;

b) heating the layer of said composition at a temperature between about 220° C. and about 350° C. to form a cross-linked pinning layer on said substrate;

c) providing a coating of a photoresist layer over said cross-linked pinning layer;

d) forming a pattern in said coating of said photoresist layer forming a patterned photoresist layer where said cross-linked pinning layer is exposed where said photoresist layer has been removed when forming said pattern in said photoresist layer;

e) etching with a plasma comprising oxygen, to remove said cross-linked pinning layer in the area where said photoresist layer has been removed and said cross-linked layer is exposed;

f) removing said patterned photoresist layer, forming a substrate with an overlying patterned cross-linked pinning layer having area regions which are covered and uncovered with cross-linked pinning layer;

g) forming a brush neutral layer at the areas of said substrate having an overlying patterned cross-linked pinning layer only in said regions on the substrate which are uncovered by the pinning layer forming a substrate with both pinning and neutral layer regions;

h) applying a block copolymer comprising an etch resistant block and highly etchable block over the neutral layer and annealing until directed self-assembly occurs; and, i) etching with a plasma said directed self-assembled layer of said block copolymer thereby removing said regions of said layer which are highly etchable overlying the substrate and forming in these regions an image in said substrate.

13. The process of claim 12 where between steps a) and b) the layer is heated at a temperature between about 80° C. and about 180° C. to remove solvent.

14. The composition of claim 1 where said random copolymer further comprises at least one styrenic repeat having structure (3),

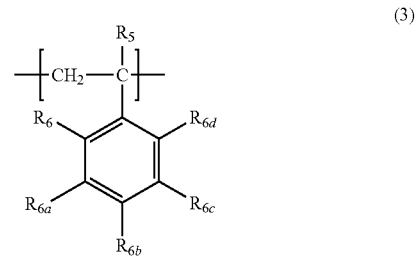

(3)

where $R_5$ is hydrogen, a C-1 to C-4 alkyl, or a C-1 to C-4 fluoroalkyl, $R_6$, $R_{6a}$, $R_{6b}$, $R_{6c}$ and $R_{6d}$ are independently selected from the group consisting of hydrogen, a C-1 to C-20 alkyl, a C-1 to C-20 alkoxy, a C-1 to C-10 fluoroalkyl, a C-1 to C-10 fluoroalkoxy, a trialkylsilyl group, a (trialkylsilyl)alkylene group, and a (trialkylsilyl)alkyleneoxy group.

15. A pinning directing layer for aromatic polymer block domains of a block copolymer overlying the pinning directing layer formed by coating a composition of claim 14 on a substrate and crosslinking it, where said pinning directing layer has a total mole % of structure (3) equal or greater than about 60 mole %, and further where the total mole % composition of repeat units of structures (1) and (3) in the random copolymer does not exceed 100 mole %.

16. A neutral directing layer for a block copolymer comprised of aromatic polymer block domains and polar aliphatic block domains overlying wherein this neutral directing layer is formed by coating a composition of claim 14 on a substrate and crosslinking it, where said neutral directing layer has a total mole % of structure (1) and structure (2) which ranges from about 45 mole % to about 55 mole % and where structure (3) ranges from about 45 mole % to about 55 mole %, and further where the total mole % composition of repeat units of structure (1), (2) and (3) in the random copolymer does not exceed 100 mole %, where $R_3$ is hydrogen, a C-1 to C-4 fluoroalkyl or a C-1 to C-4 alkyl, $R_4$ is a C-1 to C-20 alkyl, a halide, a C-1 to C-10 fluoroalkyl group, or a (trialkylsilyl)alkylene group,

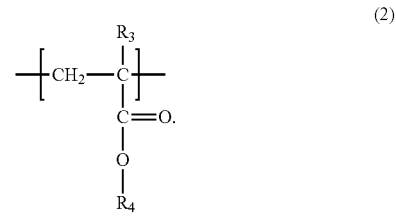

(2)

17. A process for forming an image in substrate by chemoepitaxy comprising:

a) forming a layer by coating the composition of claim 14 on a substrate forming a layer of said composition;

b) heating said layer of said composition at a temperature between about 220° C. and about 350° C. to form a cross-linked pinning layer on said substrate;

c) providing a coating of a photoresist layer over said cross-linked pinning layer forming a photoresist layer overlying said crosslinked layer on said substrate;

d) forming a pattern in said coating of said photoresist layer forming a patterned photoresist layer where part of the said photoresist layer overlying said cross-linked pinning layer in said pattern has been removed;

e) etching with a plasma comprising oxygen, to remove said cross-linked pinning layer in the area where said overlying photoresist layer has been removed;

f) removing said patterned photoresist layer, forming a substrate with an overlying patterned cross-linked pinning layer having area regions which are covered and uncovered with cross-linked pinning layer;

g) forming a brush neutral layer at the areas of said substrate having an overlying patterned cross-linked pinning layer only in said regions on said substrate which are uncovered by the pinning layer; forming a substrate with both pinning and neutral layer regions;

h) applying a block copolymer layer comprising an etch resistant block and highly etchable block over said substrate with both pinning and neutral regions and annealing said block copolymer layer until directed self-assembly occurs forming a directed self-assembled layer of said block copolymer with regions which are etch resistant and other regions which are highly etchable; and, etching the block copolymer, thereby removing said regions of said layer which are highly etchable overlying the substrate and forming in these regions an image in said substrate.

18. The composition of claim 1 where,
(ib) $R_1$ is selected from a group consisting of H and methyl,
(iib) $R_2$ is H; and
(iiib)G the alkylene moiety in structure (I) is a C-2 to C-5 alkylene moiety

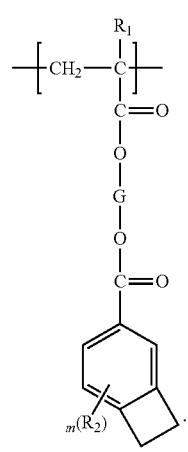

(1)

19. The composition of claim 1 where $R_1$ is H.
20. The composition of claim 1 where $R_1$ is methyl.
21. The composition of claim 1 where $R_2$ is H.
22. The composition of claim 1 where G is a C-2 to C-5 alkylene moiety.
23. A pinning directing layer for polar aliphatic polymer block domains of a block copolymer overlying the said pinning directing layer, wherein said pinning directing layer is formed by coating a composition of claim 1 on a substrate and crosslinking it, where said pinning directing layer has a total mole % of (meth)acrylate derived repeat units of structure (1), where $R_1$ is methyl, or H, and other (meth) acrylate derived repeat units is equal or greater than about 60 mole %, and further where the total mole % composition of said methacrylate derived repeat units of structure (1) and other methacrylate derived repeat units in the random copolymer does not exceed 100 mole %.

24. A process for forming a cross-linked layer on a substrate comprised of steps a) to b)
a) coating the composition of claim 1 on a substrate to form a layer;
b) heating said layer at a temperature between about 220° C. and about 350° C. to form said cross-linked layer.

25. The process of claim 24 where between steps and a) and b) the layer is heated at a temperature between about 80° C. and about 180° C. to remove solvent.

26. A process for forming a self-assembly block copolymer comprised of steps a) to d)
a) coating the composition of claim 1 on a substrate to form a layer;
b) heating said layer at a temperature between about 220° C. and about 350° C. to form a cross-linked directing layer;
c) applying a block copolymer layer over said cross-linked directing layer;
d) annealing said block copolymer layer.

27. The process of claim 26 where between steps and a) and b) the layer is heated at a temperature between about 80° C. and about 180° C. to remove solvent.

28. A process for forming an image on a substrate by chemoepitaxy comprising steps a) to h):
a) coating the composition of claim 1 on a substrate to form a layer of said composition on said substrate,
b) heating said layer of said composition at a temperature between 220° C.-350° C. to form a cross-linked neutral layer on said substrate;
c) providing a coating of a negative photoresist layer over said cross-linked neutral layer;
d) forming a pattern in said negative photoresist layer to remove the unexposed negative photoresist layer, thereby forming an uncovered cross-linked neutral layer region;
e) treating said uncovered cross-linked neutral layer region with a plasma comprising oxygen to remove the uncovered cross-linked neutral layer,
f) removing the photoresist, forming a pattered neutral layer
g) applying a block copolymer layer comprising an etch resistant block and highly etchable block over said patterned neutral layer and annealing until directed self-assembly of said block copolymer layer occurs forming a directed self-assembled layer of said block copolymer with regions of this layer which are etch resistant and other regions which are highly etchable overlying the substrate; and,
h) etching with a plasma said directed self-assembled layer of said block copolymer thereby removing said regions of said layer which are highly etchable overlying the substrate and forming in these regions an image in said substrate.

29. The process of claim 28 where between steps a) and b) said layer of said composition is heated at a temperature between about 80° C. and about 180° C. to remove solvent.

* * * * *